(12) United States Patent
Delaloye et al.

(10) Patent No.: US 12,427,020 B2
(45) Date of Patent: Sep. 30, 2025

(54) CATHETER DELIVERY SYSTEM FOR STENT VALVE

(71) Applicant: Boston Scientific Limited, Hamilton (BM)

(72) Inventors: Stephane Delaloye, Bulach (CH); Jean-Luc Hefti, Cheseaux-Noreaz (CH); Fabien Lombardi, Ecublens (CH); Pierre Simonin, Montflovin (FR)

(73) Assignee: Boston Scientific Limited, Hamilton (BM)

( * ) Notice: Subject to any disclaimer, the term of this patent is extended or adjusted under 35 U.S.C. 154(b) by 0 days.

(21) Appl. No.: 18/430,076

(22) Filed: Feb. 1, 2024

(65) Prior Publication Data

US 2024/0164900 A1    May 23, 2024

Related U.S. Application Data

(63) Continuation of application No. 16/902,386, filed on Jun. 16, 2020, now abandoned, which is a
(Continued)

(30) Foreign Application Priority Data

Oct. 13, 2014 (EP) .................................. 14188714
Dec. 8, 2014 (EP) .................................. 14196855

(51) Int. Cl.
*A61F 2/24* (2006.01)
*A61B 90/00* (2016.01)
(Continued)

(52) U.S. Cl.
CPC ............ *A61F 2/2436* (2013.01); *A61B 90/39* (2016.02); *A61F 2/2427* (2013.01); *A61F 2/95* (2013.01);
(Continued)

(58) Field of Classification Search
CPC ................ A61B 90/39; A61B 2090/08; A61B 2090/0811; A61F 2/2427; A61F 2/2436;
(Continued)

(56) References Cited

U.S. PATENT DOCUMENTS 6,733,489 B2    5/2004  Nutting et al.
8,052,732 B2   11/2011  Mitchell et al.
(Continued)

FOREIGN PATENT DOCUMENTS

JP    2011510706 A    4/2011
WO   2009053497 A1    4/2009
(Continued)

OTHER PUBLICATIONS

International Search Report and Written Opinion, dated Apr. 20, 2016, for International Application No. PCT/EP2015/07327.
(Continued)

*Primary Examiner* — Jocelin C Tanner
(74) *Attorney, Agent, or Firm* — Seager, Tufte & Wickhem LLP

(57) ABSTRACT

A delivery catheter for a stent. The delivery catheter may have a distal end and a proximal end. The distal end includes a stent attachment region adapted to receive a stent. The stent may be of the self-expanding type. The catheter further includes a handle at its proximal end and at least one sheath which may at least partially circumferentially cover the stent such as to retain it in a collapsed configuration. The sheath is coupled at its proximal end to an actuator located on the handle portion. The catheter further includes at least one radio-opaque indicator for indicating a rotational orientation of the delivery catheter and/or the stent when observed using medical imaging during implantation of the stent.

20 Claims, 12 Drawing Sheets

Related U.S. Application Data continuation of application No. 15/519,092, filed as application No. PCT/EP2015/073727 on Oct. 13, 2015, now Pat. No. 10,709,559.

(51) Int. Cl.

| | | |
|---|---|---|
| *A61F 2/95* | (2013.01) | |
| *A61F 2/966* | (2013.01) | |
| *A61F 2/97* | (2013.01) | |
| *A61M 25/01* | (2006.01) | |

(52) U.S. Cl.
CPC ............... *A61F 2/966* (2013.01); *A61F 2/97* (2013.01); *A61M 25/0108* (2013.01); *A61B 2090/0811* (2016.02); *A61B 2090/3966* (2016.02); *A61F 2/9517* (2020.05); *A61F 2250/0087* (2013.01); *A61F 2250/0089* (2013.01); *A61F 2250/0097* (2013.01); *A61F 2250/0098* (2013.01)

(58) Field of Classification Search
CPC .......... A61F 2/95; A61F 2/9517; A61F 2/966; A61F 2/97; A61F 2250/0087; A61F 2250/0089; A61F 2250/00; A61M 25/0108
USPC ....................................................... 623/2.11
See application file for complete search history.

(56) References Cited

U.S. PATENT DOCUMENTS

| | | | |
|---|---|---|---|
| 9,119,717 | B2 | 9/2015 | Wang et al. |
| 9,770,329 | B2 | 9/2017 | Lane et al. |
| 10,188,536 | B2 | 1/2019 | Lombardi et al. |
| 10,376,359 | B2 | 8/2019 | Essinger et al. |
| 10,799,351 | B2 | 10/2020 | Wang et al. |
| 2001/0051822 | A1 | 12/2001 | Stack et al. |
| 2003/0149465 | A1 | 8/2003 | Heidner et al. |
| 2004/0064128 | A1 | 4/2004 | Raijman et al. |
| 2004/0098081 | A1* | 5/2004 | Landreville ............... A61F 2/91 623/1.11 |
| 2005/0113902 | A1* | 5/2005 | Geiser ....................... A61F 2/95 623/1.11 |
| 2006/0253186 | A1* | 11/2006 | Bates ....................... A61F 2/013 623/1.11 |
| 2007/0213813 | A1 | 9/2007 | Von Segesser et al. |
| 2007/0270932 | A1 | 11/2007 | Headley et al. |
| 2008/0021313 | A1 | 1/2008 | Eidenschink et al. |
| 2008/0051867 | A1 | 2/2008 | Davila et al. |
| 2008/0172119 | A1 | 7/2008 | Yamasaki et al. |
| 2009/0076584 | A1* | 3/2009 | Mao .......................... A61F 2/91 623/1.11 |
| 2009/0259286 | A1 | 10/2009 | Ohri et al. |
| 2009/0259305 | A1 | 10/2009 | Lane et al. |
| 2010/0125322 | A1 | 5/2010 | Fitzgerald et al. |
| 2012/0083877 | A1 | 4/2012 | Nguyen et al. |
| 2012/0158129 | A1 | 6/2012 | Duffy et al. |
| 2012/0277845 | A1* | 11/2012 | Bowe ................. A61M 25/0068 623/1.11 |
| 2012/0303112 | A1 | 11/2012 | Armstrong et al. |
| 2013/0204344 | A1* | 8/2013 | Tatalovich .............. A61F 2/962 623/1.12 |
| 2013/0231736 | A1* | 9/2013 | Essinger ............... A61F 2/2436 623/2.11 |
| 2013/0338752 | A1* | 12/2013 | Geusen ..................... A61F 2/95 623/1.11 |
| 2014/0243953 | A1* | 8/2014 | Stante ..................... A61F 2/966 623/2.11 |
| 2014/0276644 | A1 | 9/2014 | Nelson |
| 2014/0296971 | A1 | 10/2014 | Tegels et al. |

FOREIGN PATENT DOCUMENTS

| | | |
|---|---|---|
| WO | 2012032147 A2 | 3/2012 |
| WO | 2013016107 A1 | 1/2013 |
| WO | 2014162306 A2 | 10/2014 |

OTHER PUBLICATIONS

Extended Search Report dated Sep. 23, 2022 for Application No. 22183126.6.

International Preliminary Report on Patentability, dated Apr. 18, 2017, for International Application No. PCT/EP2015/073727.

* cited by examiner

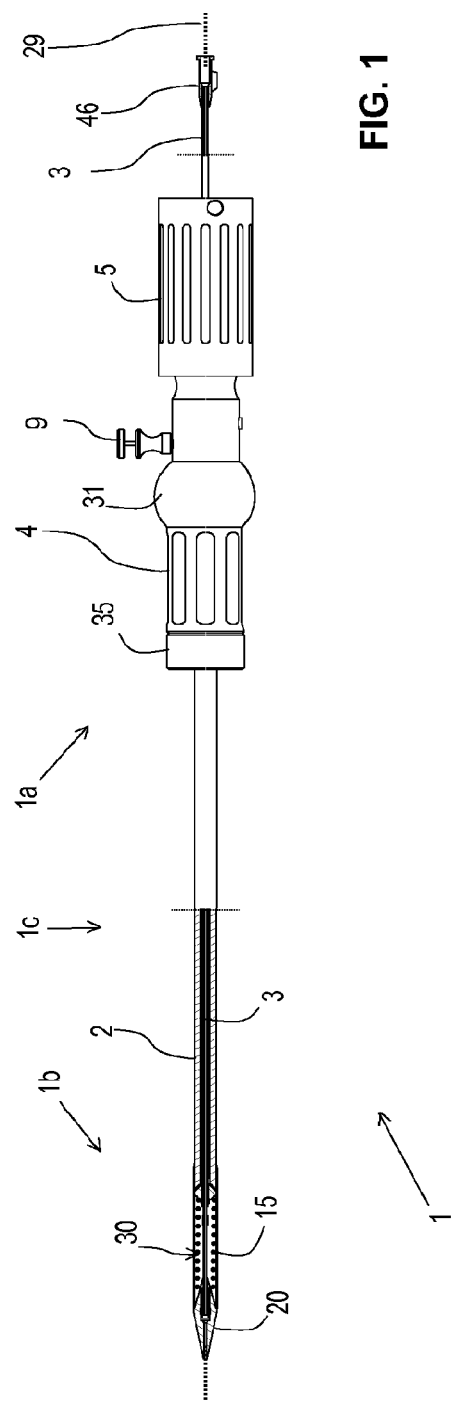
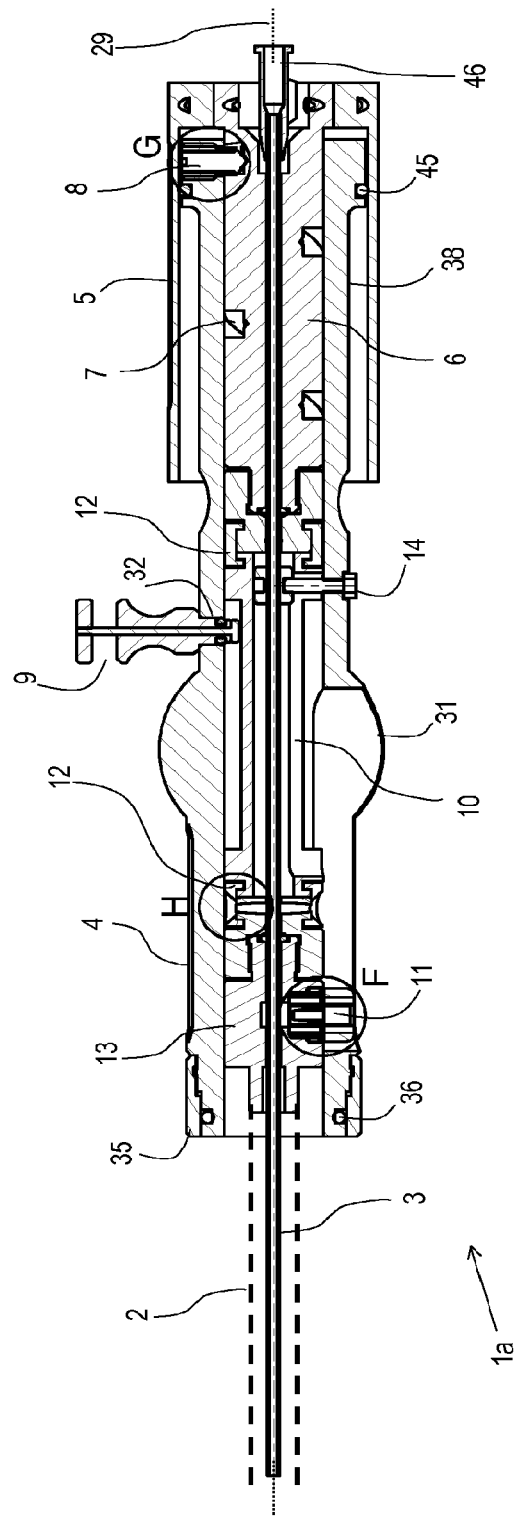
FIG. 1
FIG. 2

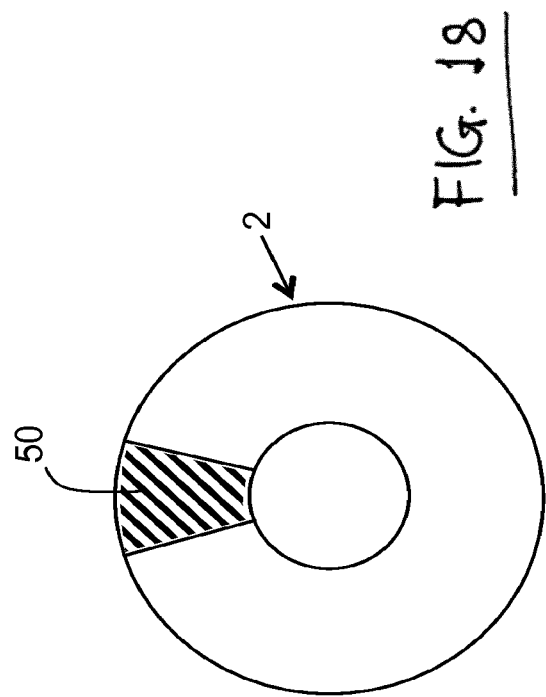
FIG. 17
FIG. 18

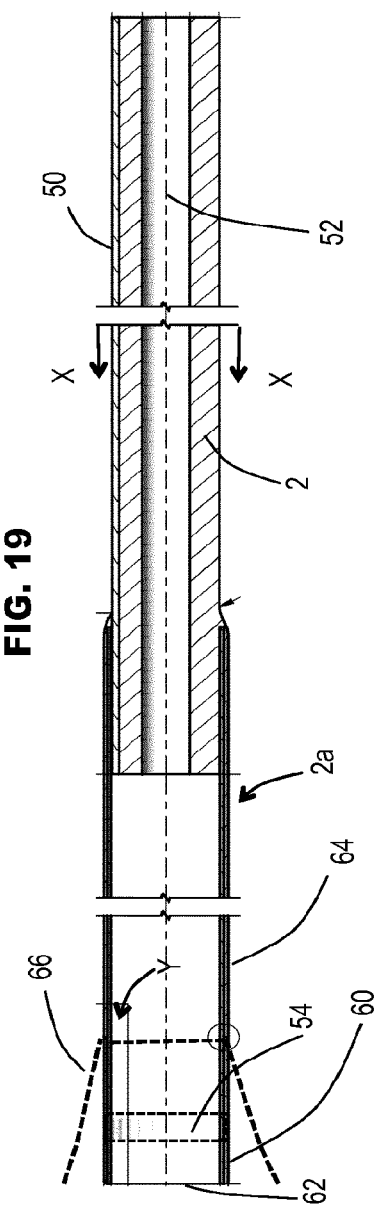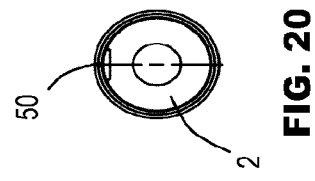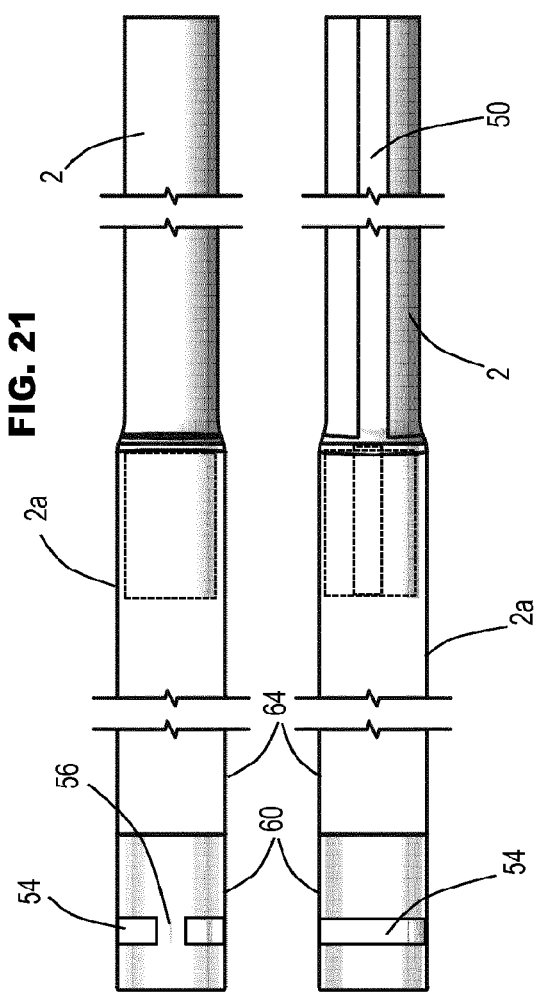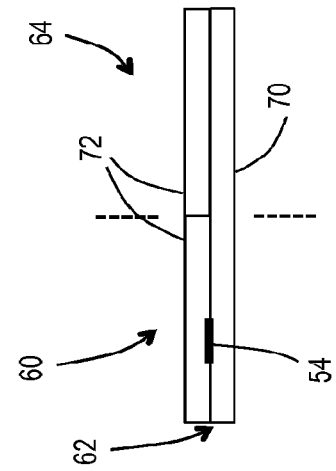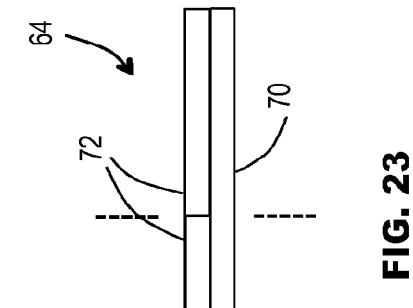

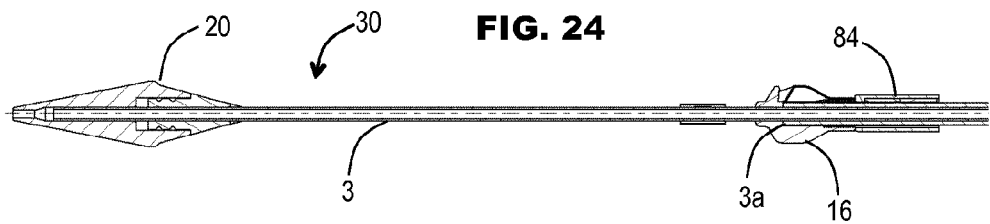
FIG. 24
FIG. 25
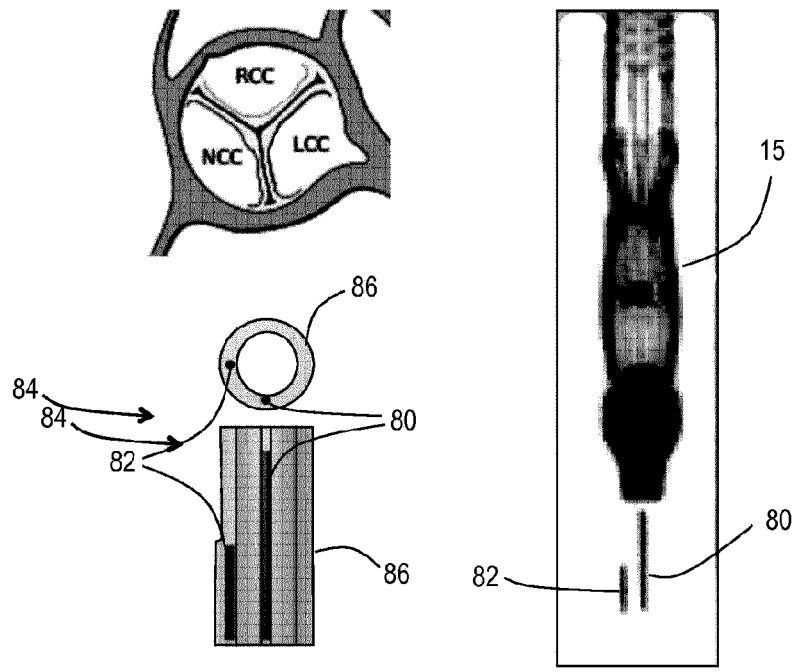
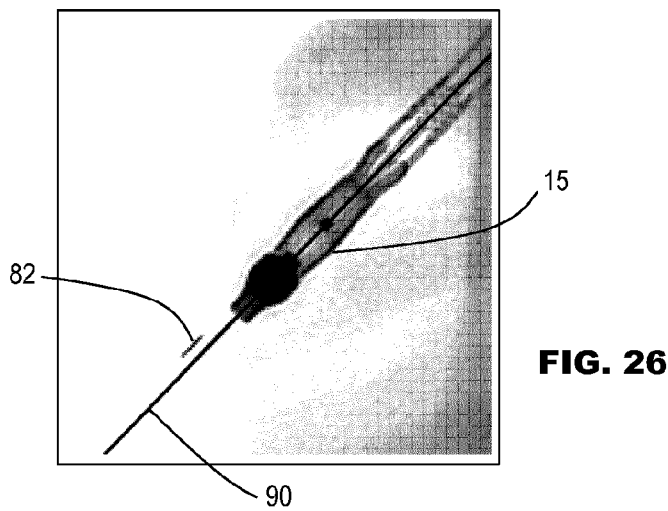
FIG. 26

CATHETER DELIVERY SYSTEM FOR STENT VALVE

CROSS-REFERENCE TO RELATED APPLICATIONS

The present application is a continuation of U.S. application Ser. No. 16/902,386, filed Jun. 16, 2020, which is a continuation of U.S. application Ser. No. 15/519,092 filed Apr. 13, 2017, now U.S. Pat. No. 10,709,559, which is a 371 of PCT/EP2015/073727 filed Oct. 13, 2015. The present application incorporates herein by reference the disclosures of each of the above-referenced applications in there entireties.

FIELD OF THE DISCLOSURE

The present disclosure relates to catheter delivery systems for stent valves according to the independent claims.

BACKGROUND TO THE DISCLOSURE

Conventional approaches for cardiac valve replacement require the cutting of a relatively large opening in the patient's sternum ("sternotomy") or thoracic cavity ("thoracotomy") in order to allow the surgeon to access the patient's heart. Additionally, these approaches require arrest of the patient's heart and a cardiopulmonary bypass (i.e., use of a heart-lung bypass machine to oxygenate and circulate the patient's blood). In recent years, efforts have been made to establish a less invasive transcatheter cardiac valve replacement procedure, via either a transvascular approach, i.e. delivering the new valve through the femoral artery, or by transapical route, where the replacement valve is delivered between ribs and directly through the wall of the heart to the implantation site.

Valve stents for use within a human body usually comprise a valve component and a stent component. The stent component is configured to house at least a portion of the valve component. According to some known proposals (see e.g. WO 2009/053497), the stent component further includes a lower anchoring crown comprising an at least partly conical body, the lower anchoring crown defining the proximal end of the stent component. The stent component further comprises an upper anchoring crown in communication with the lower anchoring crown and comprising an at least partly conical body, whereby the conical body of the lower anchoring crown slopes outwardly in the direction of the proximal end, and the conical body of the upper anchoring crown slopes outwardly in the direction of the distal end. A conical or cylindrical commissural post section is located distally of the distal end of the upper anchoring crown. Further distally, a stabilization arch section is comprised. WO 2012/032147 describes an example of delivery catheter for introducing an expandable stent-valve to the patient's heart.

While less invasive and arguably less complicated, percutaneous heart valve replacement therapies (PHVT) still face various challenges, including ease of use of a delivery system for the replacement valve, which can directly influence the inability for a surgeon to ensure proper positioning and stability of the replacement valve within the patient's body.

SUMMARY OF THE DISCLOSURE

It may be desirable to provide a catheter delivery device for stent valves avoiding the shortcoming known in the art and specifically to provide a delivery catheter system allowing for a simple and effective use, to facilitate accurate positioning and deployment of a stent valve. Some of the following description refers generally to a stent while some embodiments illustrate a stent in the form of a stent-valve. References to a stent may be read optionally as referring to a stent-valve, and vice-versa.

Broadly speaking, one aspect of the disclosure provides a delivery catheter for a stent (e.g. stent-valve). The delivery catheter may comprise a distal end and a proximal end. The distal end includes a stent accommodation region for receiving a stent. The stent may optionally be of the self-expanding type.

In some embodiments, the delivery catheter may comprise one or more radio-opaque indicators for indicating a rotational orientation of the delivery catheter and/or stent (e.g. stent-valve) when observed using medical-imaging (e.g. x-ray imaging, such as fluoroscopy) during implantation of a stent.

Such a radio-opaque indicator can provide the operator with valuable information about the rotational orientation with respect to the native anatomy. This can enable the operator, if desired, to be able to orientate the catheter and/or stent with respect to the native anatomy, even if individual stent features, or the stent orientation, are not easy to identify from the stent alone. For example, the stent in its collapsed or compressed form, may be so small and/or so deformed compared to its expanded configuration, that the orientation may be difficult to discern from the stent alone. In some embodiments, the stent may be a stent-valve, and the radio-opaque indicator(s) may be configured to enable the operator to discern whether (or when) the stent-valve is in a certain alignment with native valve anatomy.

In some embodiments, at least one radio-opaque indicator may be in fixed alignment with a stent-holder of the delivery catheter. For example, the radio-opaque indicator may indicate a rotational orientation of the stent-holder (or of a feature of the stent-holder for engaging the stent or stent-valve).

In some embodiments, the radio-opaque indicator may be spaced from the stent holder, and/or distinct from the stent holder, and/or non-integral with the stent holder. For example, the radio-opaque indicator may be spaced axially from the stent holder. Such an arrangement may permit the radio-opaque indicator to be observed more easily in the image, distinct from the relative clutter of the stent holder and attached stent of the stent-valve. It may also permit the radio-opaque indicator to be of a material different from the stent-holder, and/or be mounted on support tubing of the delivery catheter by a different mounting technique. For example, the stent holder may be secured by crimping and the radio-opaque marker(s) secured by a different technique (e.g. by mounting in carrier that is adhered to the support tubing).

In some embodiments, at least one visual indicator also provides a visual indication of the same rotational orientation as the radio-opaque marker(s). At least one radio-opaque indicator and at least one visual indicator may be provided by the same material and/or element of the delivery catheter. At least a portion of the indicator outside the body may, for example, be observed visually. At least a portion of the (e.g. same) indicator within the body may, for example, be observed by virtue of its radio-opaque property and using medical imaging.

Whether or not visual indicators are provided, in some embodiments, at least one radio-opaque indicator may comprise a feature that is substantially elongate in an axial direction of the delivery catheter. For example, the indicator may comprise an elongate line extending in a direction parallel to an axis of the catheter. The line may optionally be offset from the axis of the catheter.

In some embodiments, plural radio-opaque indicators and/or features of different length may be provided. The rotational position may be represented by the pattern presented by the indicators in combination in the observed image.

In some embodiments, the radio-opaque indicator(s) may be provided on support tubing adjacent to the stent holder.

In some embodiments, at least one radio-opaque indicator may be provided on, or comprised as part of, a stem portion of the delivery catheter, extending at least between a proximal portion of the delivery catheter (for example, a handle portion for manipulation by an operator) and a distal portion (for example, the stent accommodation region).

Additionally or alternatively, in some embodiments, at least one radio-opaque indicator may comprise a feature that extends generally circumferentially around the axis of the delivery catheter, and includes one or more patterns defining the rotational orientation. For example, the pattern(s) may be interruption(s) or discontinuity(ies) in the circumferential extent of the feature, or axial extension(s) or projection(s) of the feature. For example, at least one pattern may comprise at least one interruption or discontinuity. In one example, a circular band having a single interruption may have a generally C-shape.

In some embodiments, a combination of a first elongate feature (e.g. as a first radio-opaque indicator), and a second circumferential feature (e.g. as a second radio-opaque indicator) may be provided. The second feature may have an interruption that is offset from the first feature (for example, circumferentially by about 180 degrees). The offset may enhance the ease with which the rotational orientation can be discerned using, for example, fluoroscopy or X-ray imaging. For example, if the interruption cannot be seen (or e.g. cannot be seen clearly) in the image, then it may be in the background (e.g. obscured by the foreground), indicating that the first feature is in the foreground; alternatively, if the interruption can be seen (or e.g. can be seen clearly), then the interruption may be in the foreground, and the first feature in the background. Additionally or alternatively, by turning the delivery catheter in one direction, the corresponding movement in the fluoroscopic image can be observed to indicate which feature (e.g. the first feature or the interruption in the second feature) is in the foreground, and which is in the background.

In some embodiments, at least one radio-opaque indicator may be formed by co-extrusion of radio-opaque material with plastics tubing for forming a component of the delivery catheter. The component may, for example, be the stem referred to above. Example radio-opaque materials suitable for co-extrusion include, for example, barium sulphate and/or bismuth oxide.

Additionally or alternatively, in some embodiments, at least one radio-opaque indicator may be a metal or metal alloy that is carried on or integrated in the delivery catheter, for example, in or on a sheath for covering the stent accommodation region. An example radio-opaque metal alloy is, for example, platinum-iridium. The metal or metal-alloy may, for example, be provided in generally flat strip form (e.g. a band or split band), or in other forms such as a wire.

Additionally or alternatively to any of the aforementioned, a sheath of the delivery catheter may have a mouth region that comprises a radio-opaque indicator for indicating an axial and/or rotational position of the mouth region of the sheath. The radio-opaque indicator may comprise a pattern including at least one circumferential interruption or discontinuity. The radio-opaque indicator may have a shape comprising at least one of: generally circumferentially extending; predominantly circumferentially extending; split-ring shaped; C-shaped; an axial extent of less than about 5 mm.

Regardless of the shape, the radio-opaque indicator may have an axial extent selected as at least one from: less than about 5 mm; less than about 4 mm; less than about 3 mm, less than about 2 mm; between about 1 mm and about 2 mm.

The radio-opaque indicator may comprise at least one body of metal or metal alloy. An example metal alloy may comprise at least one of: platinum and iridium, optionally both (for example, a platinum-iridium alloy).

The mouth region may be configured to flare in response to a radially outward force exerted thereon from a stent at the stent-accommodation region, e.g. when overlapped by the mouth region. Such flaring may facilitate translation of the sheath over a stent by removing or avoiding a concentration of force at the mouth region. The circumferential interruption may be configured to permit circumferential expansion of the mouth region of the sheath during flaring. Additionally, or alternatively, the radio-opaque indicator may be spaced from a peripheral edge of the mouth region, for example, to facilitate flaring of the mouth region, especially the peripheral edge.

A second portion of the sheath, for example, adjacent to the mouth region, may be configured substantially not to flare in response to a radially outward force exerted thereon from a stent at the stent-accommodation region. The second portion may radially constrain a stent at the accommodation region.

The radio-opaque indicator may be embedded within a laminate structure of the mouth portion of the sheath.

Additionally or alternatively to any of the aforementioned, a delivery catheter for a stent-valve may comprise tubing carrying a stent holder, the stent holder having a crimp connection to the tubing.

The term "crimp connection" may refer to a folded or compressed portion of the stent holder, which forms an interference connection with the tubing. The crimp connection may be permanent in the sense that the stent holder is not removable from the tubing in normal use of the delivery catheter. Optionally, the tubing extends substantially from a stent accommodation region of the catheter to an operator handle (also referred to herein as a handle portion). The tubing may be composed of one or more components.

The crimp connection may retain the stent holder in a fixed position, axially and/or rotatably, with respect to the tubing. A crimp connection may provide a reliable and firm connection using low-cost materials, and able to withstand significant forces between the tubing and the stent holder in use (for example, significant forces during crimping of a stent-valve around the tubing, and/or during re-collapsing of a partially expanded stent-valve for "recapture" during an implantation procedure).

The stent holder may comprise one or more regions having a non-smooth surface and/or non-smooth profile that grips the tubing. For example, the non-smooth surface may bite against and/or bite into the tubing. The non-smooth surface may optionally comprise one or more of: projections; corrugations, teeth (e.g. individual teeth, or an elongate fin having a pointed section shape or a pointed tip); a helical thread. Other non-smooth surface configurations are also envisaged.

The tubing may be of plastics and/or polymeric material. Additionally or alternatively, the stent-holder may be of metal (or metal alloy); or the stent holder may be of plastics and/or polymeric material.

The stent holder may comprise a hub including one or more crimp zones of material having a radial thickness smaller than one or more adjacent non-crimp zones of material, the crimp zones defining folded or compressed regions.

The stent holder may include, at least in a region thereof, a sequence of crimp and non-crimp zones alternating with each other in a circumferential direction. Additionally or alternatively, the stent holder may include a generally annular shaped non-crimp zone. The annular non-crimp zone may, for example be at one end of the stent holder, and/or optionally correspond to or at least overlap axially with at least one stent attachment region of the stent holder.

The stent-holder may comprise one or more stent attachment regions for attachment to attachment elements of a stent-valve, for example, mating attachment. By way of example only, the attachment regions may comprise one or more projections and/or one or more recesses or sockets.

In some embodiments, any of the aforementioned concepts of the radio-opaque indicator(s) may be combined with one or more of the following features, which are all optional:

(i) The catheter further comprises a handle (also referred to as handle portion) at its proximal end and at least one sheath which may at least partially circumferentially cover said stent such as to retain it in a collapsed configuration. The sheath is coupled at its proximal end to an actuator located on said handle portion. The delivery catheter may further comprise one, or any combination of two or more, of the following features (which are all optional):

(il) The actuator may comprise a manual rotary control (also referred to herein as a rotary handle part) arranged such as to move the sheath in the distal and/or proximal direction (s) in response to rotation thereof. The actuator may comprise a single rotary control. Optionally, the rotary control is coaxial with, and/or configured to rotate around, a longitudinal axis of the catheter.

In some embodiments, the single rotary control is configured to drive translation (e.g. linear translation) of the sheath over a full operative range of movement of the sheath.

In some embodiments, the actuator is configured to drive translation of the sheath from a (e.g. fully) closed position to a (e.g. fully) open position by three complete turns or less of the rotary control, optionally two complete turns or less (measured in quarter turns, e.g., ¼ turn, ½ turn, complete turn, etc.). The translation of the sheath may be at least 50 mm, or at least 60 mm, or at least 70 mm. Such a relatively large translation of the sheath for relatively few turns of the rotary control may involve a relatively coarse thread pitch of a threaded element for converting the rotary movement into linear translational movement. The delivery catheter may optionally comprise a friction member for resisting rotation of the rotary control. The friction member may comprise a protuberance or member carried on at least one of confronting surfaces of a handle housing and the rotary control. For example, the friction member may be provided on an outer surface of the handle housing, and/or an inner surface of the rotary control. Such positioning can provide a relatively large friction-generating contact area, facilitate ease of construction and provide predictable control of the amount of friction generated. In some embodiments, the friction member comprises an O-ring, for example, of elastomeric material.

In some embodiments, the rotary control has an elongate shape (e.g. its axial length is longer than its diameter, for example at least twice as large).

In some embodiments, the rotary control has an axial length of at least 3 cm, or at least 4 cm, or at least 5 cm, or at least 6 cm, or at least 7 cm, or at least 8 cm, or at least 9 cm, or at least 10 cm.

Such sizes can facilitate intuitive gripping in the hand, for example, cupping the rotary control with the fingers and/or palm. The outer shape of the rotary control may be generally cylindrical and/or generally drum-like.

(iii) The rotary control may be configured to translate linearly with respect to a handle housing as the rotary control is rotated. Such translation progressively exposes indicia on the housing and/or control, the indicia indicating an extent of displacement of the sheath at the distal end. Such an arrangement provides an operator with an important indication of the state of the distal end of the delivery catheter. A surgeon may use this indication (optionally in combination with live-imaging of the implantation site, such as live x-ray imaging) to better monitor and control the stent implantation procedure.

In some embodiments, the rotary control may translate linearly in unison with translation of the sheath. The indicia may be a full-scale (e.g. life size) representation of the position or state of the sheath at the distal end.

In some embodiments, indicia on the handle are repeated, to be presented at least two different positions around the circumference of the handle, or at least three such different positions, or at least four different such positions. This may permit the indicia to be easily visible independently of a rotational orientation of the handle. Alternatively, the indicia may comprise one or more annular closed and/or split ring-shaped markings visible from substantially any orientation of the handle.

(iv) Additionally or alternatively, the stent carried by the delivery catheter comprises a first portion and a second portion intended to be deployed in respective first and second distinct deployment phases. For example, the first and second portions may be intended to fit on opposite sides of the annulus of an existing (e.g., native) valve. The first portion may be supra-annular and the second portion may be sub-annular. Additionally or alternatively, the first and second portions may comprise opposed crowns and/or oppositely divergent portions.

In some embodiments, the handle of the delivery catheter comprises indicia associated with movement of the actuator, for indicating at least one limit position associated the first and/or second deployment phases. A surgeon may use this indication (optionally in combination with live-imaging of the implantation site, such as live x-ray imaging) better to monitor and control the stent implantation procedure. In particular, the surgeon may, by checking the indicia, know how close the delivery catheter is to reaching the end of a respective deployment phase. Such information may be less evident from live imaging alone. This may enable the surgeon better to adapt the speed of deployment.

In some embodiments, indicia on the handle are repeated, to be presented at least two different positions around the circumference of the handle, or at least three such different positions, or at least four different such positions. This may permit the indicia to be easily visible independently of a rotational orientation of the handle. Alternatively, the indicia may comprise one or more annular closed and/or split ring-shaped markings visible from substantially any orientation of the handle.

(v) The handle may have a profile including a bulbous, e.g rounded, portion providing a tactile positioning guide for an operator's hand. The handle may optionally comprise a single bulbous portion.

The rounded bulbous portion may have a radial height, compared to at least one adjacent surface of the handle, of at least 5 mm, at least 6 mm, at least 7 mm, or at least 8 mm. The rounded bulbous portion may have an axial extent of any of: at least 20 mm; at least 25 mm; at least 30 mm. Additionally or alternatively to any of the above, the rounded bulbous portion may have an axial extent of: not greater than 40 mm; not greater than 30 mm; not greater than 35 mm.

The rounded portion may have a part-spherical and/or frusto-spherical shape. The rounded portion may have a radius of curvature of any of: at least 15 mm; at least 20 mm; at least 23 mm. Additionally or alternatively to any of the above, the radius of curvature may optionally be: not greater than 60 mm; not greater than 50 mm; not greater than 40 mm; not greater than 30 mm; not greater than 25 mm; not greater than 23 mm.

Such arrangements can provide a highly intuitive and versatile tactile positioning guide for the handle. The guide may fit snugly in the palm of the hand, and/or be cupped comfortably by the fingers. The guide may also provide a suitable surface for gripping with the fingers to apply axial force to the handle. The guide may also provide substantially the same feel to the operator whatever the rotational orientation of the handle around the catheter axis.

In some embodiments, the actuator may be distinct from the rounded bulbous portion.

The rounded bulbous portion may be an integral part of the handle and/or a housing forming at least a portion of the handle.

(vi) In some embodiments, the handle may be generally radially symmetrical. For example, the handle may be absent any cantilever handle grips. This may enable the delivery catheter to be versatile for use with any rotational orientation about the catheter axis, without the orientation making the handle more awkward to hold, manipulate or observe. This may be especially advantageous where the stent has a non-predetermined rotational orientation with respect to the delivery catheter and/or where the delivery catheter may need to be rotated about its longitudinal axis for aligning the stent with respect to the native anatomy. For example, the handle may have a generally round cross-section profile.

In some embodiments, indicia on the handle are repeated, to be presented at least two different positions around the circumference of the handle, or at least three such different positions, or at least four such different positions. This may permit the indicia to be easily visible independently of a rotational orientation of the handle. Alternatively, the indicia may comprise one or more annular closed and/or split ring-shaped markings visible from substantially any orientation of the handle.

(vii) The handle may further comprise at least one indicator rotatable about a catheter axis. The indicator may be positionable to indicate a rotational alignment of a stent (e.g., stent-valve) with respect to the handle. The indicator may be manually positionable.

This aspect of the disclosure may enable the operator to set a convenient indication of the rotational alignment of the stent. In some embodiments, the rotational orientation of the stent may be variable or non-predetermined with respect to the delivery catheter. For example, the stent may have a variable or non-predetermined orientation with respect to a stent holder of the attachment region. Additionally or alternatively, the stent holder may have a non-predetermined orientation with respect to the handle. However, although the orientation may be non-predetermined, it may be unlikely to change after loading of the stent into the delivery catheter. The orientation may be visible during and/or following loading, allowing the indicator to be set accordingly to provide an indication useful for the implantation procedure. Once the distal end has been inserted into the body, the distal end (and the stent) is no longer directly visible. The operator may have access to live imaging (e.g. x-ray imaging) from which the rotational orientation may be deduced. However, the provision of an indicator directly at the handle can provide a direct and intuitive indication of the orientation to further assist the operator, and remove any ambiguity from the x-ray imaging.

In some embodiments, the stent is a valve stent (also referred to as a stent-valve) comprising a valve having valve leaflets meeting at, and/or supported at, a plurality of peripheral commissures. The indicator may comprise indicia for indicating the rotational orientation of the commissures. The indicator may comprise plural indicia, e.g. one for each commissure.

The indicator may comprise a rotatable collar mounted towards a distal end of the handle. The rotatable collar may bear indicia (e.g. laser inscribed indicia, or indicia members embedded at least partly within the collar).

(viii) The delivery catheter may further comprise a stem portion extending between the handle and the distal portion. The stem portion may have a flexure characteristic such that, in order to produce flexure displacement of 10 mm using a three-point bending test, the applied force is between 2.5 and 7.5 N (inclusive range). The three-point bending test may comprise supporting the stem portion at two spaced apart positions, and observing the degree of bending displacement (e.g., with respect to a straight axis) when a force is applied, in a diametrically opposed direction to the supports, at a position midway between the spaced apart support positions. The test may be carried out at room temperature.

Optionally, the defined range of applied force may be associated with a spacing between the supports that is between about 16 and about 20 times the outer diameter of the stem.

In one example, the spacing between the supports may be 20 times the outer diameter of the stem. The applied force may be between 2.5 and 4.5 N. Optionally the applied force may be at least 2.6 N, optionally at least 2.7 N, optionally at least 2.8 N, optionally at least 2.9 N, optionally at least 3.0 N, optionally at least 3.1 N, optionally at least 3.2 N, optionally at least 3.3 N, optionally at least 3.4 N, optionally at least 3.5 N, optionally at least 3.6 N, optionally at least 3.7 N, optionally at least 3.8 N, optionally at least 3.9 N, optionally at least 4.0 N. Additionally or alternatively to any of the above, the applied force may optionally be no greater than 4.0 N, optionally no greater than 3.9 N, optionally no greater than 3.8 N, optionally no greater than 3.7 N, optionally no greater than 3.6 N, optionally no greater than 3.5 N, optionally no greater than 3.4 N, optionally no greater than 3.3 N, optionally no greater than 3.2 N, optionally no greater than 3.1 N. Optionally, the applied force may be between about 3.0 N and about 3.7 N In another example, it may not be practical to using a spacing of 20 times the outer diameter of the stem if (for example), the stem as used in the delivery device is shorter than would be needed for such measurement. For example, the outer diameter may be about 9.8 mm (+−0.5 mm), and the available length for measurement may be about 160 mm. In that case, the ratio of the distance (spacing) divided by the outer diameter is about 16. For such an example (spacing 160 mm and/or outer diameter of 9.8 mm (+−0.5 mm) and/or a spacing of about 16 times the outer diameter, the applied force may be between about 6.0 and about 7.5 N. Optionally, the applied force may be at least 6.1 N, optionally at least 6.2 N, optionally at least 6.3 N, optionally at least 6.4 N, optionally at least 6.5 N, optionally at least 6.6 N, optionally at least 6.7 N, optionally at least 6.8 N, optionally at least 6.9 N, optionally at least 7.0 N, optionally at least 7.1 N, optionally at least 7.2 N, optionally at least 7.3 N, optionally at least 7.4 N. Additionally or alternatively to any of the above, the applied force may optionally be no greater than 7.4 N, optionally no greater than 7.3 N, optionally no greater than 7.2 N, optionally no greater than 7.1 N, optionally no greater than 7.0 N, optionally no greater than 6.9 N, optionally no greater than 6.8 N, optionally no greater than 6.7 N, optionally no greater than 6.6 N, optionally no greater than 6.5 N, optionally no greater than 6.4 N, optionally no greater than 6.3 N, optionally no greater than 6.2 N, optionally no greater than 6.1 N. Optionally, the applied force may be between about 6.5 and about 7.0 N Such flexure characteristics may be advantageous in meeting the conflicting desirata of flexibility and support. Especially in the case of a transapical approach, the delivery catheter has to provide sufficient support to be able to advance the distal end through a relatively tight access aperture in the ventricle wall. It is desirable that the aperture in the ventricle be as small as possible, to reduce risk of interference with the distribution of natural electrical pulses essential to healthy heart operation, and/or reduce the invasiveness of the procedure on the heart tissue, and/or facilitate easier closing after the procedure to restore the integrity of the ventricle wall, and/or facilitate the patient's recovery after the procedure. It is desirable to create the access aperture undersized, and rely on the elasticity of the heart muscle tissue to allow the aperture to expand elastically to accommodate passage of the delivery catheter therethrough. Such a tight fit can also provide a self-seal against blood leakage, the procedure being carried out while the heart remains beating to pump blood around the circulatory system. However, the delivery catheter has to support application of force from the proximal end to drive the distal portion through such an undersized aperture. The delivery catheter also has to be flexible to accommodate a non-straight delivery path through the heart and the existing valve. Additionally, different surgeons have different preferences for the entry path through the anatomy to the heart. For example some surgeons prefer a relatively flat entry along a direction close to the patients body, while others prefer a more inclined path. A stiff catheter can provide excellent support, but without flexibility the catheter may not accommodate the non-straight delivery path, but may be difficult to introduce and position, and may not achieve optimum positioning of the prosthetic valve. The flexure characteristic defined herein can provide a surprisingly good balance between the two.

The three point bending test parameter as defined above is used because, in the some embodiments, the stem portion comprises plural tubes nested one within the other, with or without a substantial clearance therebetween. A small flexure might only involve flexing of one tube. The above parameter can provide a consistent parameter applicable to the entire stem portion instead of only a single tube.

(ix) In some embodiments, the distal end is intended to be inserted into a human body, such as into the heart and/or circulatory system. The proximal end is intended to stay outside of the patient and to allow manipulation of the catheter by an operator, e.g. a surgeon. The distal and the proximal end are thereby connected by a stem or trunk portion, comprising at least one tubular member.

As understood herein, the terms "distal" and "proximal" define the orientation of an element from the operator of the delivery device. Therefore, the "proximal end" is the end of the catheter device which is nearer to the operator, while the "distal end" is farther away.

At the distal end, the catheter delivery system includes a stent attachment region. In some embodiments, the stent attachment region comprises retaining means such as to retain the stent on the catheter at a defined longitudinal position. This allows the user to advance the catheter through a portion of the heart of a patient, e.g. through a ventricle, or through the vasculature of a patient, e.g. through the aorta, without the danger that the stent might slip off the catheter. In some embodiments, the retaining means are thereby configured in such a way as to release the stent during or just after its expansion.

The stent used in connection with the catheter delivery system according to the present disclosure may be of the self-expanding type. Such stents are known in the art and are made of or comprise a superelastic material such as a Nickel-Titanium alloy, e.g. available under the name Nitinol. Alternatively the stent might also be made of or comprise other metallic materials, such as metallic materials exhibiting some elasticity. Further alternatively, the stent might also be deployable by means of a balloon or the like.

The catheter delivery device further comprises a handle portion located at its proximal end. The handle portion provides means for an operator to hold and operate the catheter delivery system. These may include handles, knobs, buttons, trigger elements, etc.

Further, the delivery device comprises at least one sheath. Said sheath may at least partially circumferentially cover the stent. By covering the stent, the sheath holds the stent in a collapsed configuration, such that the stent may be introduced into the circulatory system. In some embodiments, the sheath completely covers the stent during insertion. Once the stent is positioned at the right place, e.g. over the aortic valve, the sheath may be moved proximally over the stent, thereby sequentially uncovering the stent. The portions of the stent which are uncovered are thereby free to expand.

For this purpose, the sheath is coupled to an actuator located on said handle. The coupling thereby is either direct or indirect, depending on the kind of actuator used. Especially in the case where the actuator comprises a rotational movement, an element transforming said rotational movement into a translational movement may be arranged between the sheath and the actuator. The element may, for example, be threaded. The thread may be helical.

In some embodiments, the actuator in the catheter delivery system according to the present disclosure consists of a single rotary handle or handle part. This handle (part) is thereby arranged in such a way as to move the sheath either in the distal or in the proximal direction. In some embodiments, the rotary handle (part) is configured in such a way as to move the sheath both in the distal and in the proximal direction, for example, depending on the direction of rotation of the actuator. This offers the advantage that the sheath may not only be moved over the stent along the proximal direction thereby releasing the stent, but also along the distal direction thereby re-capturing the stent and/or facilitating loading of the stent into the delivery catheter. In some embodiments, it may be possible to revert certain expanded portions of the stent into the collapsed configuration. This may allow repositioning of a stent if needed.

The rotary handle (part) may be configured in any suitable way. In some embodiments, the rotary handle (part) is in the form of a cylinder arranged at the proximal end of the handle. Alternatively, the rotary handle may also be configured as knob or crank.

(x) The delivery catheter includes gear means providing for at least two different transmission or gear ratios between the movement of actuation means and the movement of the sheath, depending on the position of the distal end of the sheath along the stent and/or with respect to the attachment region.

The gear means allow for at least two different gear ratios between the movement of the actuation means and the movement of the sheath. The gear ratio thereby is the proportion between the distance that the distal end of the sheath is moved in comparison to the distance that the actuation means has been moved. For example, in the case of a rotary handle, a constant gear ratio would mean that for every turn of the handle the distal end of the sheath would move along the same distance. As soon as a gear means with at least two different gear ratios depending on the position of the distal end of the sheath along the stent is used, the distal end of the sheath moves a certain first distance for every turn of the handle with the first gear ratio and a second distance different from the first distance for every turn of the handle with the second gear ratio. The second distance may be bigger or smaller than the first distance.

A low gear ratio means that the distal end of the sheath will move a shorter distance along the stent compared to the movement of the actuation means. Taking a rotary handle as an example, this means that the distance which the distal end of the sheath moves for every turn of the handle will be shorter than with a higher gear ratio.

Such a configuration allows providing a catheter delivery system having different unsheathing characteristics depending on which portion the distal end of the sheath is being moved. Specifically, the delivery device can be configured such that a small gearing ratio is provided when the distal end of the sheath is moving along portions of the stent requiring slower and/or more accurate deployment.

The gear means also provides a kind of feedback mechanism to the operator. The force needed to move the sheath will be higher with a high gear ratio compared to a low gear ratio. In the case of a rotary handle, this translates into a higher torque to be applied to the handle. This can readily be sensed by an operator or alternatively be measured by an instrument.

In some embodiments, the catheter delivery device according to the present disclosure comprises a single rotary handle as actuation means, whereby said rotary handle is arranged such as to move the sheath both in the distal and the proximal direction, wherein a gear means is arranged between said rotary handle and the proximal end of said sheath.

Alternatively, the actuation means may also comprise a trigger element moveable in the distal and the proximal direction. The trigger element is thereby configured such as to move the sheath element in the distal and/or the proximal direction, wherein a gear means is arranged between the proximal end of the sheath and the trigger element.

In some embodiments, said gear means is configured such that when the sheath is moved in the proximal direction to unsheath the stent, the gearing means provides a different gear ratio, such as a higher gear ratio when the sheath moves along a first portion of the stent compared to the gear ratio provided when it moves along a second portion of the stent located proximally to said first portion.

When used in combination with a valve stent intended for trans-apical insertion, this means that unsheathing and hence deployment of the distal part of the stent located in the aorta will take place with a high gear ratio. Especially but not exclusively in the case that the most distal parts usually do not serve to anchor the stent but rather comprise stabilizing means, the operator needs a less precise control of the deployment. Further, a high gear ratio enables a quicker deployment as compared with a lower gear ratio. The more proximal portions of the stent may comprise one or more anchoring crowns. Especially but not exclusively in the case that it is important to have a correct placement and orientation of the stent when deploying the anchoring crown or crowns, it is advantageous to use a low gear ratio, as this enables the operator to have a more accurate control on the deployment. Further, the deployment speed will also be lower, thereby reducing the risk of miss orientation of the crown. As the force needed to move the sheath is also lower when using a lower gear ratio, re-capture of the stent may be easier.

In some embodiments, said gear means is further configured such that the gear ratio provided when the sheath moves along said second portion of the stent is different (e.g., lower), compared to the gear ratio provided when the sheath moves along a third portion of the stent located proximally to said second portion.

In some embodiments, the most proximal portion of the stent comprises attachment elements adapted to be coupled to the retaining means located on the catheter. The coupling may be configured in such a way as to provide for a de-coupling of the stent as soon as its most proximal portion expands. This may e.g. be achieved by providing loops on the most proximal portion of the stent which are mounted on pins provided on the catheter. As long as the stent is held in its collapsed configuration, the pins remain within the loops, thereby realisably coupling the stent to the catheter. As soon as the stent expands, the loops will slip over the pins thereby uncoupling the stent from the catheter. Alternatively, any other suitable coupling means may be used.

As it is favourable that all coupling means are decoupled simultaneously such as to not lead to a miss orientation of the stent, it is desirable that the distal end of the sheath may be moved quicker along the most proximal portion of the stent than along the foregoing portions. This is achieved by providing a higher gear ratio.

In some embodiments, the gear means comprises a cylindrical threaded element having at least two regions with a different thread pitch.

The thread pitch is the distance along the longitudinal axis between two crests of the thread. As the threaded element according to the present disclosure has a single thread, the pitch corresponds to the lead. Therefore the pitch may also be defined as the advancement of the sheath for each turn of the threaded element.

Providing a gear means with a cylindrical threaded element provides for a simple and easy to use catheter delivery device. In one embodiment, the cylindrical threaded element may be provided within the handle and may be directly coupled to the actuation means provided as rotary handle. On the inside of the handle, a pin may be provided which engages the thread. In an alternative embodiment, the thread may be provided on the inner side of a rotary actuation means provided as hollow cylinder. The sheath is thereby coupled to a pin which engages the thread. Further, any other suitable configuration may be used.

The thread may be provided with any suitable profile. In some embodiments, the thread has a rectangular or rounded profile. Alternatively, the thread may also comprise a triangular profile.

The pin which is engaged into the thread may comprise a rolling ball at its tip, thereby reducing the friction force between the pin and the thread.

The threaded element comprises a thread with a greater pitch in a first region compared to the pitch in a second region, said greater pitch allowing a greater gear ratio when the sheath moves along the first portion than along the second portion of the stent.

In a further embodiment, the threaded element comprises a thread with a greater pitch in a third region compared to the pitch in the second region, said greater pitch allowing a greater gear ratio when the sheath moves along the third portion of the stent than over the second portion.

This allows providing a catheter delivery system with a gear means comprising different gear ratios.

Further, alternatively, the gear means is configured such that different gear ratios are provided when the sheath moves along the second portion of the stent, such as by providing a varying pitch on the second region of the threaded element.

This provides for different sensitivities and/or unsheathing speeds when deploying the central portions of a stent. E.g. the gear ratio may be varied for deployment of the upper and/or the lower crown of the stent.

In some embodiments, the cylindrical threaded element is exchangeable. As such, it is possible to easily vary the combination of gear ratios, and especially to provide specific combinations for different stent application methods and/or stent sizes.

(xi) The catheter comprises feedback or braking means (e.g., tactile feedback means) to indicate when the distal end of the sheath has reached a defined position on the stent during proximal and/or distal movement of said sheath along said stent or to cause a braking effect when the distal end of the sheath has moved beyond a certain position along the stent.

The feedback means may be tactile means. This allows the operator to sense when the distal end of the sheath has reached a defined position. As the feedback means have a direct influence on the movement the operator uses to deploy the stent, the feedback will be more direct than if other feedback means, such a light or sound signal were used. Advantageously, the feedback means warn the operator that the distal end of the sheath is about to move over the proximal end of the stent.

Alternatively, a catheter delivery device according to the present disclosure may comprise more than one feedback and/or braking means, such as two, three or more defining various predetermined intermediate positions.

In one embodiment, said feedback means comprise at least one removable pin or stop limiting the movement of said distal end of the sheath beyond a certain position on the stent. Once the distal end of the sheath reaches the defined position, no further movement will be possible until the stop is removed. Alternatively, an element may be provided which does not completely stop the movement, but which may be pushed out, e.g., against the force of a spring. As the removal of the pin or stop by moving the actuation means further will require some additional force, the operator will have a tactile feedback.

In an alternative embodiment, the feedback means may be formed as a braking means comprising an element applying an additional resistance to the actuation means once the distal end of the sheath moves beyond a certain point on the stent. This may be achieved by means of additional friction forces acting on the actuation means or the sheath. The resistance may alternatively also be applied by a gear means.

Further, alternatively, the feedback or braking means may comprise a threaded element with a varying thread pitch, wherein a decrease of said thread pitch increases the resistance of the actuation means. Such a feedback or braking means is especially advantageous on catheter delivery devices where the actuation means consist of a trigger element.

Said feedback means may be arranged such as to avoid movement of the sheath beyond a position on said stent beyond which an increased risk of unwanted self-deployment of the stent exists.

Once the distal end of the sheath is near the proximal end of the stent, there is a certain risk that the stent pushes itself out of the sheath by means of the expansion force. This may lead to an unwanted release of the stent before it is correctly oriented and placed. To avoid such a premature release, the movement of the distal end of the sheath beyond a certain point where this risk exists may be stopped or slowed down by the feedback or braking means.

Broadly speaking, a further independent aspect of the disclosure relates to a stop that is removably engageable with a delivery catheter for blocking or resisting deployment movement of a portion of the catheter for deploying a stent therefrom, at least beyond a predetermined deployment position. The deliver catheter may optionally include any of the aforementioned features. The removable stop may comprise first and second parts movable relative to each other.

The removable stop may optionally further comprise any one or any combination of two or more of the following features (which are all optional):

(i) The first and second parts may be arranged one part for bearing a removal force, and the other part for bearing at least a portion of an opposite reaction to the removal force.

Such a stop is highly advantageous by reducing, to a large extent, the reaction to the removal force applied to the delivery device itself. For example, if using a traditional pull-out friction-fit pin, the surgeon has to support the delivery device with one hand in order to support the reaction to the force applied with the other hand to pull-out the pin. Similarly, if using a screw threaded pin, the surgeon has to support the delivery device with one hand to support the reaction to the unscrewing force applied with the other hand to the pin. Unscrewing may also be inconvenient during an implantation procedure. In both cases, the reaction to the removal force is applied to the delivery device, and there is a risk that minor movements of the delivery catheter handle when transmitted to the stent at the distal end, may have undesirable effects. For example, the stent may be partly deployed and/or be in operative contact with the anatomy. Minor movement can sometimes cause accidental release of the stent or displace the stent out of a desired implantation position. In contrast, with the present aspect of the disclosure, the two-part configuration of the removable stop can reduce significantly the reaction to the removal force experienced by the delivery catheter.

The first and second parts may be substantially coaxial about an axis of the stop, and slidable relative to each other along said axis.

One of the first and second parts of the stop may comprise a pull-out friction-fit within an aperture of the delivery catheter handle, and the other part may comprise a pusher for pushing against the delivery device.

(ii) The first and second parts may have spaced apart portions that, when squeezed one towards the other, are configured to release the stop from the handle.

A further independent aspect of the disclosure provides a method of using a delivery catheter for implanting a stented prosthetic aortic valve, the delivery catheter having a distal portion comprising: a tip member and a sheath movable with respect to the tip member, the distal portion carrying the prosthetic aortic valve constrained by the sheath, the sheath having a closed position in which the sheath abuts the tip member; the method comprising:
(a) advancing the distal portion within a patient's anatomy towards the implantation site;
(b) subsequently partly displacing the sheath with respect to the tip member such that the sheath is spaced from the tip member, without deploying substantially the stent;
(c) subsequently further advancing the distal portion with the sheath spaced from the tip member, the spacing permitting the tip member to flex with respect to the sheath member;
(d) subsequently further displacing the sheath with respect to the tip member in order to deploy the stent.

Such a method can address an issue of the sheath, when abutting the tip member, potentially limiting the freedom of the tip member to flex. By partly displacing the sheath from the tip member, at least after having penetrated the heart and/or vascular system, the tip member can be allowed more freedom to flex at the expense of reduced support. This can be used to assist advancement of the distal portion without deploying the stent. For example, for a transapical delivery catheter, by partly displacing the sheath from the tip member after having penetrated the ventricle (such as after having passed through an existing valve), the tip member can be allowed more freedom to flex. This can assist introduction and/or advancement of the distal portion in the ascending aorta and/or in the aortic arch, especially in cases where a person's individual anatomy may make such advancement difficult.

According to some embodiments, a delivery catheter for a stent is provided wherein the delivery catheter comprises a distal end and a proximal end, the distal end including a stent attachment region adapted to receive a stent, the catheter further comprising a handle at its proximal end and at least one sheath for at least partially circumferentially covering said stent such as to retain it in a collapsed configuration, the sheath being coupled at its proximal end to an actuator located on said handle for actuating movement of the sheath, the handle further comprising an indicator rotatable about the longitudinal axis of the catheter, the indicator being positionable to indicate a rotational orientation of a stent with respect to the handle. The delivery catheter of some embodiments may comprise an indicator that is manually settable. The stent may be a valve stent comprising a valve having valve leaflets and associated peripheral commissures, and wherein the indicator comprises indicia for indicating the rotational orientation of at least one of the commissures.

According to some embodiments, a delivery catheter for a stent is provided wherein the delivery catheter comprises a distal end and a proximal end, the distal end including a stent attachment region adapted to receive a stent, the catheter further comprising a handle at its proximal end and at least one sheath for at least partially circumferentially covering said stent such as to retain it in a collapsed configuration, the sheath being coupled at its proximal end to an actuator located on said handle for actuating movement of the sheath, wherein the handle comprises a bulbous portion intermediate distal and proximal ends of the handle, the bulbous portion providing a tactile positioning guide for an operator's hand.

The bulbous portion may be one or more selected from: (i) rounded; (ii) frusto-spherical; (iii) distinct from the actuator. The bulbous portion may have one or more dimensions selected from: (i) a radial height compared to at least one adjacent surface of at least 5 mm; (ii) an axial extent of at least 20 mm; (iii) a radius of curvature of at least 15 mm; (iv) a radius of curvature not greater than 60 mm.

According to some embodiments, a delivery catheter for a stent is provided wherein the delivery catheter comprises a distal end and a proximal end, the distal end including a stent attachment region adapted to receive a stent, the catheter further comprising a handle at its proximal end and at least one sheath for at least partially circumferentially covering said stent such as to retain it in a collapsed configuration, the sheath being coupled at its proximal end to an actuator located on said handle for actuating movement of the sheath, the actuator comprising a manual rotary control arranged such as to move the sheath in the distal and/or proximal direction(s) along an operative range of movement in response to rotation of the rotary control through three turns or less around the longitudinal axis of the catheter. The delivery catheter may further comprise a friction member for frictionally resisting rotation of the rotary control.

According to some embodiments, a delivery catheter for a stent is provided wherein the delivery catheter comprises a distal end and a proximal end, the distal end including a stent attachment region adapted to receive a stent, the catheter further comprising a handle at its proximal end and at least one sheath for at least partially circumferentially covering said stent such as to retain it in a collapsed configuration, the sheath being coupled at its proximal end to an actuator located on said handle for actuating movement of the sheath, the actuator comprising a manual rotary control rotatable around the longitudinal axis of the catheter and arranged such as to move the sheath in the distal and/or proximal direction(s), the rotary control having a longitudinal length of at least 4 cm. The rotary control may be elongate in the direction of the longitudinal axis of the According to some embodiments, a delivery catheter for a stent is provided wherein the delivery catheter comprises a distal end and a proximal end, the distal end including a stent attachment region adapted to receive a stent, the catheter further comprising a handle at its proximal end and at least one sheath for at least partially circumferentially covering said stent such as to retain it in a collapsed configuration, the sheath being coupled at its proximal end to an actuator located on said handle for actuating movement of the sheath, the actuator comprising a manual rotary control associated with a helical thread than causes linear translation of the rotary control relative to the handle as the rotary control is turned, the handle further comprising indicia positioned so as to be progressively exposed or covered by the rotary control according to the linear position of the rotary control, the indicia indicating an extent of displacement of the sheath at the proximal portion. The rotary control may be configured such that the linear translation of the rotary control is the same linear translation as the sheath.

According to some embodiments, an assembly is provided comprising a self-expanding stent-valve for replacing an aortic valve, and a delivery catheter of the present disclosure. The stent may comprise first and second portions configured for engagement, in use, with opposite sides of a native aortic valve annulus. The delivery catheter may comprise a distal end and a proximal end, the distal end including a stent attachment region adapted to receive the stent, the catheter further comprising a handle at its proximal end and at least one sheath for at least partially circumferentially covering said stent such as to retain it in a collapsed configuration, the sheath being coupled at its proximal end to an actuator located on said handle for actuating movement of the sheath, the actuator comprising a manual rotary control, and the handle further comprising indicia for indicating sheath displacement with respect to a first step for deploying the first stent portion and a second step for deploying the second stent portion.

According to some embodiments, a delivery catheter for a stent is provided where the delivery catheter comprises a distal end and a proximal end, the distal end including a stent attachment region adapted to receive a stent, the catheter further comprising a handle at its proximal end and at least one sheath for at least partially circumferentially covering said stent such as to retain it in a collapsed configuration, the sheath being coupled at its proximal end to an actuator located on said handle for actuating movement of the sheath, wherein a stem portion of the delivery catheter extending between said distal and proximal portions has a flexure characteristic such that, in order to produce flexure displacement of 10 mm using a three-point bending test, the applied force is between 2.5 and 7.5 N (inclusive range). The stem portion of the delivery catheter may include a tube member and a sheath member around the tube member.

According to some embodiments, a delivery catheter for a stent is provided wherein the delivery catheter comprising a distal end and a proximal end, the distal end including a stent attachment region adapted to receive a stent, the catheter further comprising a handle at its proximal end and at least one sheath for at least partially circumferentially covering said stent such as to retain it in a collapsed configuration, the sheath being coupled at its proximal end to an actuator located on said handle for actuating movement of the sheath, the delivery catheter further comprising a removable stop for obstructing actuator displacement beyond a certain position, the removable stop comprising first and second parts movable relative to one another, the first and second parts being arranged one part for bearing a removal force, and the other part for bearing at least a portion of an opposite reaction to the removal force.

According to some embodiments, a delivery catheter for a stent is provided comprising a distal end and a proximal end, the distal end including a stent attachment region adapted to receive a stent, the catheter further comprising a handle at its proximal end and at least one sheath for at least partially circumferentially covering said stent such as to retain it in a collapsed configuration, the sheath being coupled at its proximal end to an actuator located on said handle for actuating movement of the sheath, the delivery catheter further comprising a removable stop for obstructing actuator displacement beyond a certain position, the removable stop comprising first and second parts movable relative to one another and having spaced apart portions that, when squeezed one towards the other, are configured to release the stop from the handle.

According to some embodiments, a delivery catheter for delivery of a valve is provided comprising a distal end and a proximal end, said distal end including a stent attachment region adapted to receive a stent, preferably of the self-expanding type; said proximal end comprising a handle; and at least one sheath which may at least partially circumferentially cover said stent such as to retain said stent in a collapsed configuration, said sheath being coupled at its proximal end to actuation means located on said handle, characterized in that said actuation means consists of a single rotary handle part arranged such as to move said sheath in the distal and the proximal direction.

According to some embodiments, a delivery catheter for delivery of a valve stent is provided comprising a distal end and a proximal end, said distal end including a stent attachment region adapted to receive a stent, preferably of the self-expanding type; said proximal end comprising a handle portion; and at least one sheath which may at least partially circumferentially cover said stent such as to retain said stent in a collapsed configuration, characterized in that said delivery catheter further comprises gear means providing for at least two different transmission ratios between the movement of actuation means and the movement of the sheath depending on the position of the distal end of the sheath along said stent.

According to some embodiments, a delivery catheter for delivery of a valve stent is provided comprising a distal end and a proximal end, said distal end including a stent attachment region adapted to receive a stent, preferably of the self-expanding type; said proximal end comprising a handle portion; and at least one sheath which may at least partially circumferentially cover said stent such as to retain said stent in a collapsed configuration, said sheath being coupleable at its proximal end to actuation means located on said handle portion such as to be moved along said stent, characterized in that said catheter further comprises feedback means and/or braking means, preferably tactile feedback means, to indicate when the distal end of the sheath has reached a defined position on the stent during proximal and/or distal movement of said sheath along said stent and/or to cause a braking effect once the distal end of the sheath moves beyond a defined position along the stent.

According to some embodiments, a method is provided for using a delivery catheter for implanting a stented prosthetic aortic valve, the delivery catheter having a distal portion comprising: a tip member and a sheath movable with respect to the tip member, the distal portion carrying the prosthetic aortic valve constrained by the sheath, the sheath having a closed position in which the sheath abuts the tip member; the method comprising: advancing the distal portion within a patient's anatomy towards the implantation site; subsequently partly displacing the sheath with respect to the tip member such that the sheath is spaced from the tip member, without deploying substantially the stent; subsequently further advancing the distal portion with the sheath spaced from the tip member, the spacing permitting the tip member to flex with respect to the sheath member; and subsequently further displacing the sheath with respect to the tip member in order to deploy the stent. The step of advancing may comprise advancing the distal portion along a transapical path. The step of subsequently partly displacing the sheath with respect to the tip member such that the sheath is spaced from the tip member, without deploying substantially the stent may be carried out after penetrating a ventricle wall of the heart.

Further advantages and characteristics of the present disclosure are described in the following description of examples and figures. The Applicant claims protection for any novel feature or idea described herein and/or illustrated in the drawings whether or not emphasis has been placed thereon.

BRIEF DESCRIPTION OF THE DRAWINGS

For a better understanding of the present disclosure, reference is made to the following description, taken in FIG. 1 is a schematic side view of a first embodiment of delivery catheter, with selected portions shown in cross-section.

FIG. 2 is a schematic section illustrating the proximal (handle) end of the delivery catheter of the first embodiment.

FIG. 16 is a front perspective view of a delivery catheter including a radio-opaque indicator in one embodiment.

FIG. 17 is a perspective view of tubing for forming a stem of the delivery catheter of FIG. 16.

FIG. 18 is a cross-section through the tubing of FIG. 17.

FIG. 19 is a schematic section through a further example of component provided with a radio-opaque indicator.

FIG. 20 is a schematic cross-section along the line X-X of FIG. 19.

FIG. 21 is a schematic view from below of the component of FIG. 19.

FIG. 22 is a schematic view from above of the component of FIG. 19.

FIG. 23 is a schematic cross-section showing a detail of the region "Y" from FIG. 19.

FIG. 24 is a schematic cross-section showing a distal end of support tubing used in a further example of delivery catheter with radio-opaque indicators near a stent holder.

FIG. 25 is a schematic diagram illustrating the relation between a native valve implantation site (top left), the radio-opaque indicators (bottom left), and a fluoroscopic image in two-dimensional projection (right).

FIG. 26 is a schematic diagram illustrating a medical imaging view (from fluoroscopy) during an implantation procedure with a radio-opaque guidewire.

DETAILED DESCRIPTION

Figure 3:
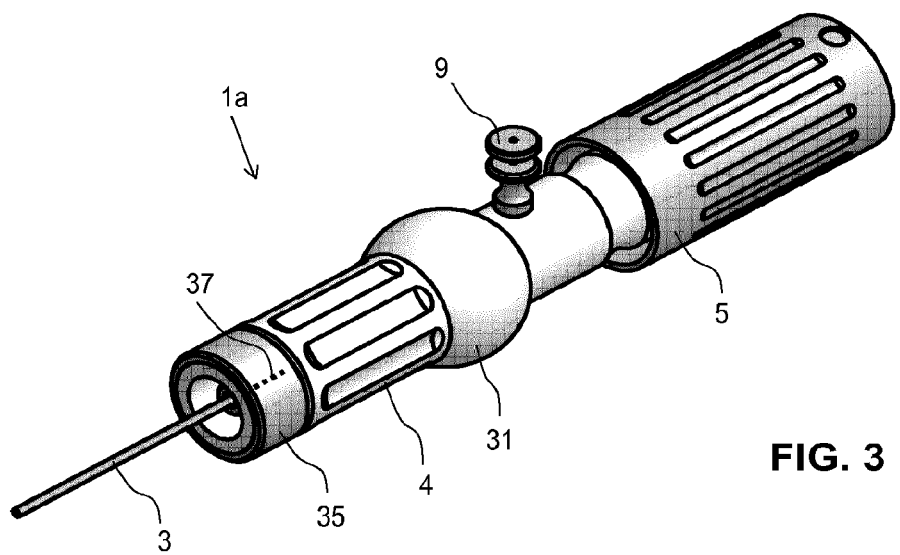
FIG. 3 is a schematic perspective view from above the proximal end (without the sheath represented).

In the following non-limiting detailed description, the same reference numerals are used to denote equivalent or similar features where appropriate. Further, reference is made to the accompanying drawings which form a part hereof, and in which is shown by way of illustration a specific embodiment in which the disclosure may be practiced. It is to be understood that other embodiments may be utilized and structural changes may be made without departing from the scope of the present disclosure.

Some embodiments of the present disclosure include at least one radio-opaque indicator, as described later with respect to FIGS. 16-26. However, detailed examples of delivery catheter are first described. It will be appreciated that the concept of a radio-opaque indicator is not limited to these detailed examples, although synergistic advantages are provided by combination.

Additionally or alternatively, some embodiments of the present disclosure include a stent holder with a crimp connection, as described later with respect to FIGS. 27-29. However, detailed examples of delivery catheter are first described. It will be appreciated that the concept of a stent holder is not limited to these detailed examples, nor to the radio-opaque indicator(s), although synergistic advantages are provided by the combination with the detailed catheter examples and/or the radio-opaque indicator(s).

FIGS. 1-14 illustrate a first embodiment of delivery catheter (also referred to as exemplary delivery device 1) for implanting a stent (e.g., valve stent or stent-valve) 15. The delivery catheter 1 comprises a proximal portion 1*a* to be held by an operator, a distal portion 1*b* for insertion into the body, and a stem or barrel portion 1*c* extending between the proximal and distal portions.

A sheath 2 may extend from the proximal portion 1*a* to the distal portion 1*b* where it may cover at least partly a stent 15 accommodated at a stent receiving portion 30, and arranged on tube member 3. Tube member 3 may further comprise a lumen adapted for the insertion of a guide wire 29. The tube member 3 may extend through a handle 4 at the proximal portion 1*a*. The handle 4 may comprise an actuator for controlling and/or driving linear translation of the sheath 2 in the proximal and/or distal direction(s). Translation of the sheath in e.g., the proximal direction may uncover the stent to deploy or allow deployment of the illustrated form, the actuator comprises a manually operable rotary control (also referred to as a rotary handle or rotary handle member) 5.

Two examples of the proximal portion 1*a* are illustrated in FIGS. 1-5, and have similar features as follows. The handle 4 may comprise a cylindrical interior lumen into which the sheath 2 may be received. A connection member 13 may be coupled to the proximal end of the sheath 2. Optionally, the connection member 13 may comprise a valve 11, which serves as inlet for a physiological saline solution used to flush the distal end of the catheter delivery device 1. A rotary member 12 may be arranged proximally to the connection member 13, e.g. to avoid the physiological saline solution to flow further towards the proximal end of the handle 4 and to rotationally support the various elements. A sliding member 10 may be arranged between rotary member 12 and a threaded cylindrical element 6. A removable stop 9 may be arranged on the handle 4, e.g. removably received in an aperture 32. The stop 9 may function to prevent proximal movement of the sheath beyond a certain point, corresponding to partial release and/or deployment of the stent 15 without complete release and deployment. The stop 9 can engage the sliding element 10 to prevent the proximal movement of said element 10, and of the sheath 2, beyond said certain point. Only after removing the stop 9 the sheath 2 may be completely removed from the stent by moving the sheath to a most proximal position. Further, a fixation element 14 may be arranged in handle 4. The fixation element 14 may serve to stabilise the tube 3 against longitudinal movement with respect to the handle 4. Fixation element 14 may engage a channel (for example defined by a pulley profile) associated with the tube 3.

The catheter delivery device 1 may further comprise gear means. The gear means include: a cylindrical threaded element 6 having a thread 7; and a pin 8. The cylindrical threaded element 6 is coupled to the rotary handle (rotary control) acting as the actuator. The pin 8 is fixed with respect to the handle 4, and the pin 8 is engaged into thread 7. Upon rotation of the actuator 5 the cylindrical threaded element 6 will also turn. As pin 8 is engaged into thread 7, the rotation of the element 6 will result in a movement of the element 6 either in the proximal or in the distal direction, depending on which way actuator 5 is turned. As the cylindrical threaded element 6 is coupled via sliding element 10, rotary element 12 and connection member 13 to the sheath 2, the translational movement of the cylindrical threaded element 6 will be transmitted to sheath 2.

The rotary handle 5 may be elongate in shape. The axial length may be longer than the diameter, for example, twice as large, or more. The rotary control may comprise an axial length of between about 3 cm to about 15 cm, 20 cm or 30 cm, including at least 3 cm, or at least 4 cm, or at least 5 cm, or at least 6 cm, or at least 7 cm, or at least 8 cm, or at least 9 cm, or at least 10 cm. Such sizes can facilitate intuitive gripping in the hand, for example, cupping the rotary control with the fingers and/or palm. The outer shape of the rotary control may be generally cylindrical and/or generally drum-like.

The tube 3 is optionally fitted at its proximal end with a luer valve 46. The rotary handle 5 may include a socket or recess for accommodating, at least partly, the shape of the luer valve 46 when the rotary handle 5 is screwed or translated proximally. (Such accommodation is illustrated schematically in FIG. 2 although for the purposes of space in the drawing the rotary handle 5 is shown screwed towards the distal portion 1*b*).

The outer profile of the handle 4 may be generally cylindrical, optionally with one or more finger grips or recesses. Additionally or alternatively, the outer profile may include at least one bulbous portion 31, e.g. partly spherical in shape. Such a portion 31 may allow more positive positioning of the handle in the hand according to individual preferences.

The bulbous 31 portion may have a radial height, compared to at least one adjacent surface of the handle, of between about 3 mm to about 10 mm, 15 mm or 30 mm, including at least 5 mm, at least 6 mm, at least 7 mm, or at least 8 mm. The bulbous portion 31 may have an axial extent of any of between about 15 mm to about 40 mm, including at least 20 mm; at least 25 mm; at least 30 mm. Additionally or alternatively to any of the above, the bulbous portion 31 may have an axial extent of: not greater than 40 mm; not greater than 30 mm; not greater than 35 mm.

The bulbous portion 31 may have a frusto-spherical shape. The bulbous portion 31 may have a radius of curvature of any of between about 10 mm to about 40 mm, 50 mm or 60 mm, including at least 15 mm; at least 20 mm; at least 23 mm. Additionally or alternatively to any of the above, the radius of curvature may optionally be: not greater than 60 mm; not greater than 50 mm; not greater than 40 mm; not greater than 30 mm; not greater than 25 mm; not greater than 23 mm.

Such arrangements of bulbous portion 31 can provide a highly intuitive and versatile tactile positioning guide for the handle. The guide may fit snugly in the palm of the hand, and/or be cupped comfortably by the fingers. The guide may also provide a suitable surface for gripping with the fingers to apply axial force to the handle. The guide may also provide substantially the same feel to the operator whatever the rotational orientation of the handle 4 around the catheter axis.

Figure 7:
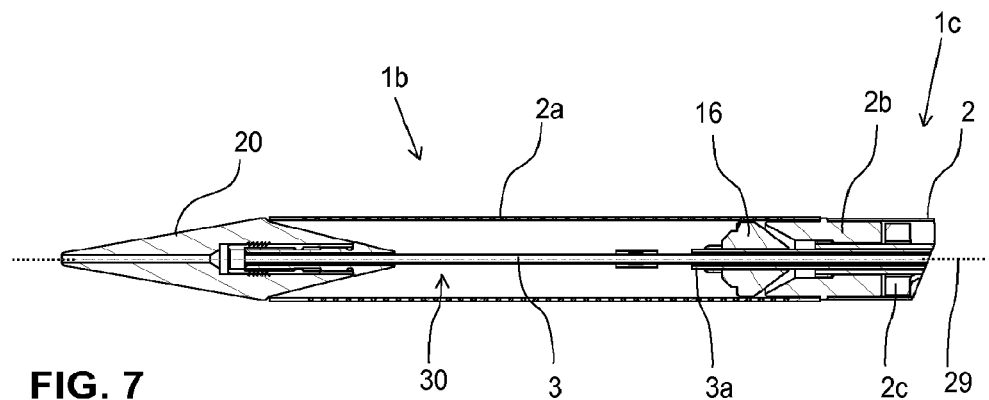
FIG. 7 is a schematic section illustrating one example of a distal end of the delivery catheter for the first embodiment.
Figure 8:
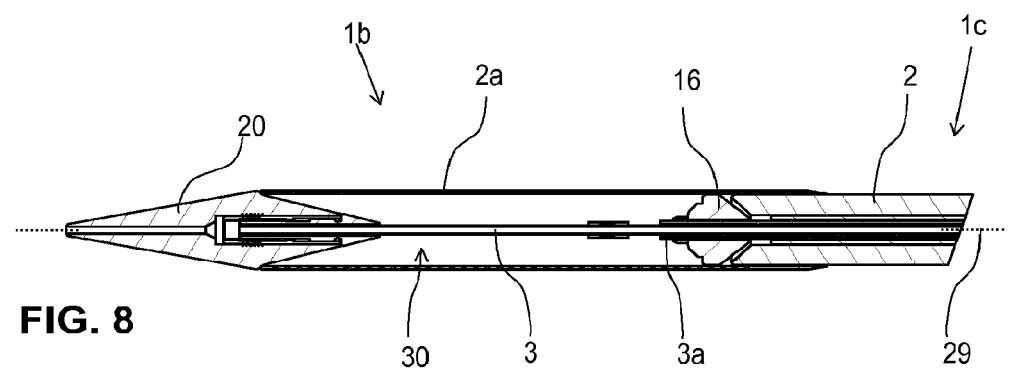
FIG. 8 is a schematic section illustrating another example of a distal end of the delivery catheter for the first embodiment.

FIGS. 7 and 8 show two examples of the distal portion 1*b* of the catheter delivery device. The examples are similar and differ only in terms of the nature of the sheath 2. In both examples, the sheath 2 comprises a constraining portion 2*a* for covering a stent at the stent receiving portion 30. The constraining portion 2*a* may be an integral extension of the sheath 2, or it may be a reinforced sheath part bonded or otherwise permanently attached to the sheath 2. In the illustrated form, the constraining portion 2*a* has substantially the same outer diameter as the sheath 2 (at least no difference larger than 10%, or more preferably no larger than 5%). Such constant size may facilitate sealing against blood leakage where the catheter penetrates the wall of a blood vessel or the heart wall, even when no introducer is used. For example, a good seal may be achieved by advancing the distal portion 1*b* through an undersized aperture in the ventricle wall. The elasticity of the ventricle wall permits passage of the distal portion 1*b* through the undersized aperture, while tightly engaging the outer surface.

The stent 15 may be coupled to the tube member 3 by coupling means (also referred to as a stent holder) 16, for preventing axial movement of the stent until the moment of full release and/or full deployment. The tube member 3 may itself be reinforced over at least a part of its length by a dual wall structure (e.g., one tube nested within another, and coupled to function as a single unit). As evident at 3*a*, the dual wall structure may optionally terminate distally of the coupling means 16, although in a modified construction shown in FIG. 24, the dual wall structure may optionally may terminate at the coupling means (stent holder) 16, or at a different position. At the most distal tip, the catheter delivery device 1 may comprise a tip element 20, for example having a conical from. The tip element 20 may allow for an easy insertion of the delivery catheter.

In the form illustrated in FIG. 7, the sheath 2 comprises (in the stem portion 1*c* of the delivery catheter) an outer tube and an annular spacer member 2*c* disposed between the outer tube 2 and the tube member 3. The annular spacer member 2*c* may be segmented and may serve to prevent kinking of the outer tube 2*b*. The outer tube 2*b* may be coupled to the constraining portion 2*a* by means of an intermediate bridge 2*b*. The bridge 2*b* may optionally form part of, or be coupled to, the annular spacer member 2*c*.

In the form illustrated in FIG. 8, the sheath 2 comprises a thicker wall tube without an annular spacer member. The thicker wall tube resists kinking.

Figure 6:
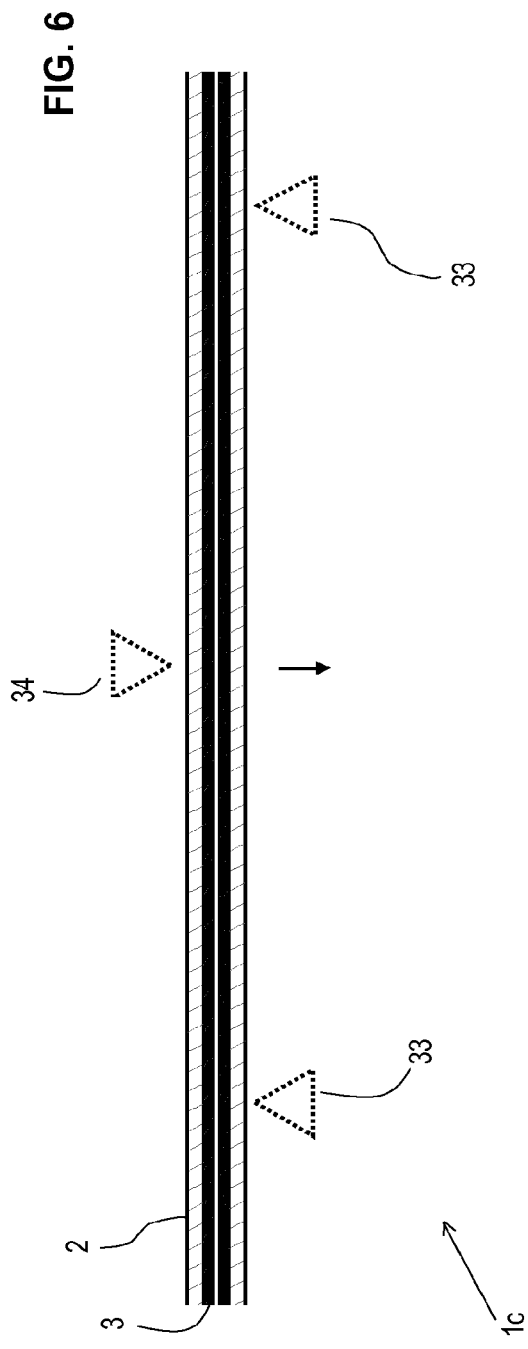
FIG. 6 is a schematic section illustrating a three-point bending test for the stem of the delivery catheter.

Referring to FIG. 6, in some embodiments the stem portion 1*c* may have a flexure characteristic such that, in order to produce flexure displacement of 10 mm using a three-point bending test, the applied force may be (i) between 2.5 and 3.5 N (inclusive range), or (ii) between about 6.0 and 7.5 N (inclusive range), or (iii) generally between about 2.5 and 7.7 N (inclusive range). The three-point bending test may comprise supporting the stem portion at two spaced apart positions 33, and observing the degree of bending displacement when a force is applied, in a diametrically opposed direction to the supports, at a position 34 midway between the spaced apart support positions. The spacing between the support positions may be about 16 to about 20 times the outer diameter of the stem. The flexure displacement may be measured as a displacement with respect to a condition of the stem 1b when no force is applied (e.g. substantially straight, or with only slight flexure). The applied force range (i) may optionally be associated with a spacing of 20 times the outer diameter. The applied force range (ii) may optionally be associated with a spacing of 160 mm and/or an outer diameter of 9.8 mm (+−0.5 mm) and/or a spacing that is about 16 times the outer diameter.

Such a flexure characteristic may be advantageous in meeting the conflicting desirata of flexibility and support. Especially in the case of a transapical approach, the delivery catheter has to provide sufficient support to be able to advance the distal end through a relatively tight access aperture in the ventricle wall. It is desirable that the aperture in the ventricle be as small as possible, to reduce risk of interference with the distribution of natural electrical pulses essential to healthy heart operation, and/or reduce the invasiveness of the procedure on the heart tissue, and/or facilitate easier closing after the procedure to restore the integrity of the ventricle wall, and/or facilitate the patient's recovery after the procedure. It is desirable to create the access aperture undersized, and rely on the elasticity of the heart muscle tissue to allow the aperture to expand elastically to accommodate passage of the delivery catheter therethrough. Such a tight fit can also provide a self-seal against blood leakage, the procedure being carried out while the heart remains beating to pump blood around the circulatory system. The delivery catheter also has to be flexible to accommodate a non-straight delivery path through the heart and the existing valve. Different surgeons have different preferences for the entry path through the anatomy to the heart. The flexure characteristic defined herein can provide a surprisingly good balance between the support and flexibility.

Figure 9:
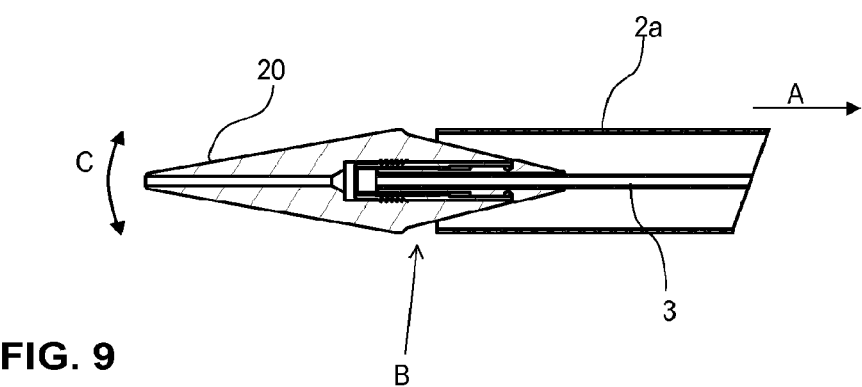
FIG. 9 is a schematic section illustrating a stage of partial opening of a distal end of a delivery catheter.

Referring to FIGS. 7-9, in some embodiments, a method is used for selectively enhancing flexibility of the distal portion 1b. As can be seen in FIGS. 7 and 8, in the closed position of the sheath 2, the sheath 2 may abut a confronting surface of the tip element 20. Such abutment may support stably the tip element 20 when the tip 20 is advanced through an undersized aperture in the ventricle wall. Once inside the heart, and/or after having advanced at least partly though the valve to be replaced, it may be desirable to allow the tip element 20 more freedom to flex. Referring to FIG. 9, in the some embodiments, this is achieved by displacing the sheath 2 partly (as indicated by arrow A), so that it no longer abuts the tip element 20 (as indicated at B), but is not sufficiently displaced to allow substantial deployment of the stent 15. Displacing the sheath 2 away from the tip element 20 removes the direct support, thereby permitting the tip 20 greater freedom to flex (indicating by arrow C). Following such partial or limited displacement, the distal portion 1b may be further advanced into the heart and/or ascending aorta, while benefiting from the enhanced flexibility of the tip, until the distal portion 1b arrives at a desired position for deployment of the stent 15. Thereafter, the sheath 2 is displaced further in the direction of arrow A to release the stent 15.

In some embodiments, the handle 4 carries an indicator 35 for indicating, to the operator viewing the proximal portion 1a of the catheter, the rotational orientation of the stent 15 carried at the distal portion 1b. Depending on the design of stent 15, it may be desirable to implant the stent with a certain rotational orientation with respect to the local anatomy. The stent 15 may have a non-predetermined, or variable, rotational orientation with respect to the stent holder 16 and/or to the handle 4. However, although the orientation may be non-predetermined, it may remain constant once the stent 15 has been loaded into the stent containing region 30 and constrained by the sheath 2. Once loaded, the operator can set the indicator 35 to indicate the orientation of the stent 15 at loading. The indicator 35 enables the operator to known the orientation of the stent, even when the distal portion 1b is hidden with the anatomy. The procedure may be carried out using medical imaging from which the stent orientation may also be derivable, but the presence of an indication directly on the handle 4 provides the operator with additional information to avoid any ambiguity. The present disclosure also envisages provision of at least one radio-opaque indicator (see FIGS. 16 and 17) on the delivery catheter to aid with orientation.

In the illustrated forms, the indicator 35 comprises a ring or collar rotatable around the axis of the handle and/or delivery catheter. The indicator 35 is manually settable by manual rotation. A friction member 36 (e.g. an O-ring of elastomeric material) frictionally resists rotation of the indicator 35, so that it is unlikely to slip out of the set position in use. In some embodiments, the indicator 35 carries or comprises visual indicia 37. For example, the indicia 37 may be printed on the indicator 35, or comprise distinct elements (e.g. as in FIG. 4).

Figure 14:
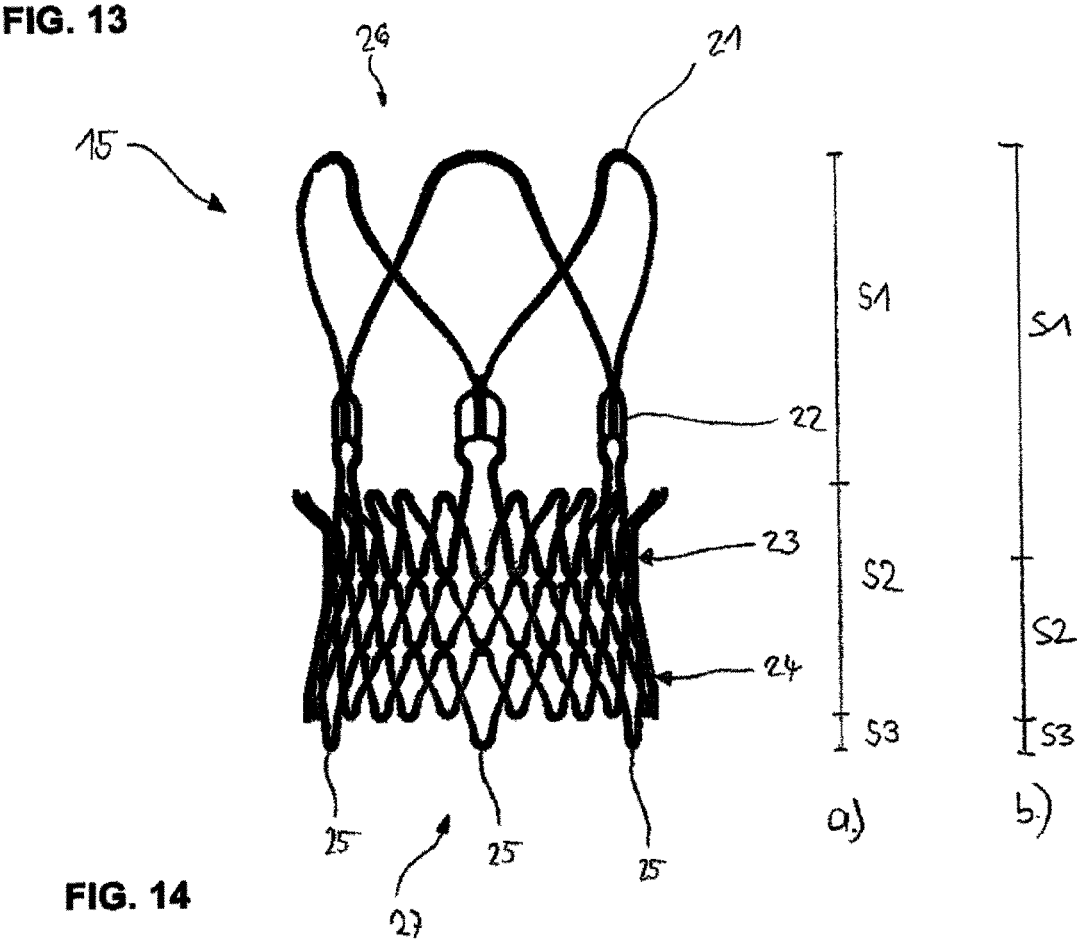
FIG. 14 is a schematic side view of an exemplary stent valve optionally used in connection with a delivery catheter according to the present disclosure.

In some embodiments, the stent 15 comprises plural commissures associated with the shape of the stent and/or the valve. The indicator 35 may bear plural indicia 37, one for each commissure. By way of example only, FIG. 14 shows one example of a stent 15 optionally used in connection with a catheter delivery device 1 of the present disclosure. The stent 15 has a distal end 26, a proximal end 27 and comprises stabilization arches 21, commissural posts 22, upper anchoring crown 23, lower anchoring crown 24 as well as attachment elements 25. The stabilization arches 21 serve to stabilize the stent 15 in a blood vessel, preferably the aorta, during deployment. Typically, three leaflets of a replacement heart valve are attached to commissural posts 22. The upper anchoring crown 23 serves to attach the stent 15 in the aortic side of a heart valve, while the lower anchoring crown serves to attach the stent 15 on the ventricular side of the heart valve. Attachment means 25 enable the removable attachment of the stent 15 to the stent holder 16 of the catheter delivery device 1. The illustrated stent 15 has three commissures, and the indicia 37 may comprise three respective indications.

In some embodiments, the delivery catheter 1 comprises feedback means for providing an indication to the operator of: (i) the sheath position (e.g. degree to the which the sheath is displaced open); and/or (ii) release state of the stent 15; and/or (iii) when the sheath reaches a predetermined release position associated with a release phase of the stent.

In some embodiments, the feedback means comprises a visual indication 38 on the handle.

Figure 10:
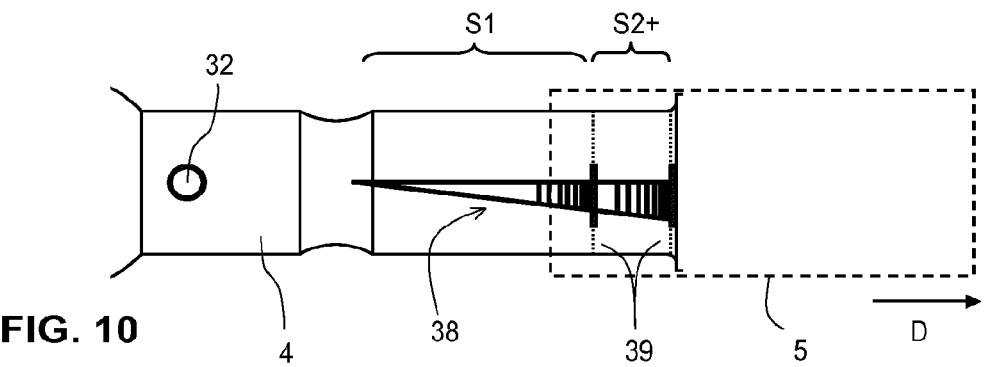
FIG. 10 is a schematic plan view illustrating indicia on the handle of the proximal end of a delivery catheter.
Figure 11:
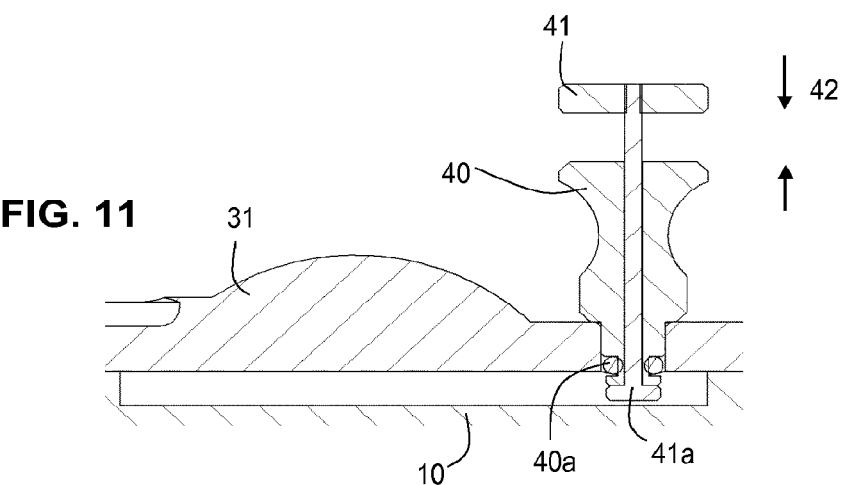
FIG. 11 is a schematic section illustrating in detail a removable stop.

Referring to FIG. 10, the indicator 38 comprises indicia on a portion of the surface of the handle 4 that is selectively covered or exposed, depending on the position of the rotary control 5. The threaded connection between the rotary control 5 and the handle 4 results in the rotary control 5 translating linearly (as indicated by arrow D) as the rotary control 5 is turned. The rotary control 4 translates linearly with the sheath 2. The linear position of the rotary control 5 thus provides a representation of the linear position of the sheath 2. The indicator 38 is provided at a position on the handle 4 such that the indicator 38 is progressively exposed by the linear translation of the rotary control 5. The indicator 38 may for example, comprise a scale indicating the extent to which the sheath 2 is open at the distal portion 1b (for example, represented by a triangular form, the spacing between the two long sides indicating the extent to which the sheath is open). Additionally or alternatively, the indicator 38 may comprise one or more marks 39 indicating when a certain release position of the sheath 2 has been achieved. For example, if the stent 15 has the form illustrated in FIG. 14 and described above, it may be intended for release in plural steps or phases S1 and S2+(which may be S2+S3 in FIG. 14). A first step S1 corresponds to the release of the stabilization arches 21 and, optionally, the upper crown 23. A second step (S2+) includes release of the lower crown 24 and, optionally, the attachment elements 25. The indication marks 39 enable the operator to see when the respective release point of each step or phase is expected to occur, and to control the delivery catheter 1 accordingly.

The indications 38 and/or 39 may be repeated at plural positions around the circumference of the handle 4, so that at least one indication 38/39 may always be in view irrespective of the rotational orientation of the handle 4. Additionally or alternatively, the indications may be circumferentially continuous (e.g., as represented by the circumferential broken lines at 39).

As mentioned previously, the removable stop 9 may also provide tactile feedback to the operator about when the sheath reaches the end of the first step S1. The removable stop 9 may be configured to obstruct further linear translation of the sheath 2 once the end of the first step S1 has been reached.

In a simple form (e.g. as in FIG. 5), the removable stop 9 may consist of a pin having a friction member (e.g. an O-ring of elastomeric material) at its end insertable into the aperture 32. In a more enhanced form (FIGS. 1-4 and 11), the removable stop 9 may consist of first and second parts 40 and 41 that are displaceable relative to each other. The first and second parts 40 and 41 may be arranged one part for bearing a removal force, and the other part for bearing at least a portion of an opposite reaction to the removal force. Such a stop is highly advantageous by reducing, to a large extent, the reaction to the removal force applied to the delivery device itself. For example, if using a pull-out friction-fit pin as in FIG. 5, the reaction force is applied to the delivery catheter, and the operator has to support the delivery catheter with one hand in order to support the reaction to the force applied with the other hand to pull-out the pin. However, minor movement or perturbation of the delivery catheter can sometimes cause accidental release of the stent or displace the stent out of a desired implantation position. In contrast, a two-part configuration 40, 41 of the removable stop 9 can reduce significantly the reaction to the removal force experienced by the delivery catheter. The first and second parts 40 and 41 may be substantially coaxial about an axis of the stop, and slidable relative to each other along said axis. One part 40 may comprise a pull-out friction-fit within the aperture 32 of the handle 4, and the other part 41 may comprise a pusher for pushing against the delivery device. The first part 40 may carry a friction member 40a (similar to that described above). The second part 41 may have a pusher tip 41a. The first and second parts 41 may have spaced apart manually engageable portions that, when squeezed one towards the other (as indicated by the arrows 42 in FIG. 9) are configured to release the stop 9 from the handle 4.

Figure 12:
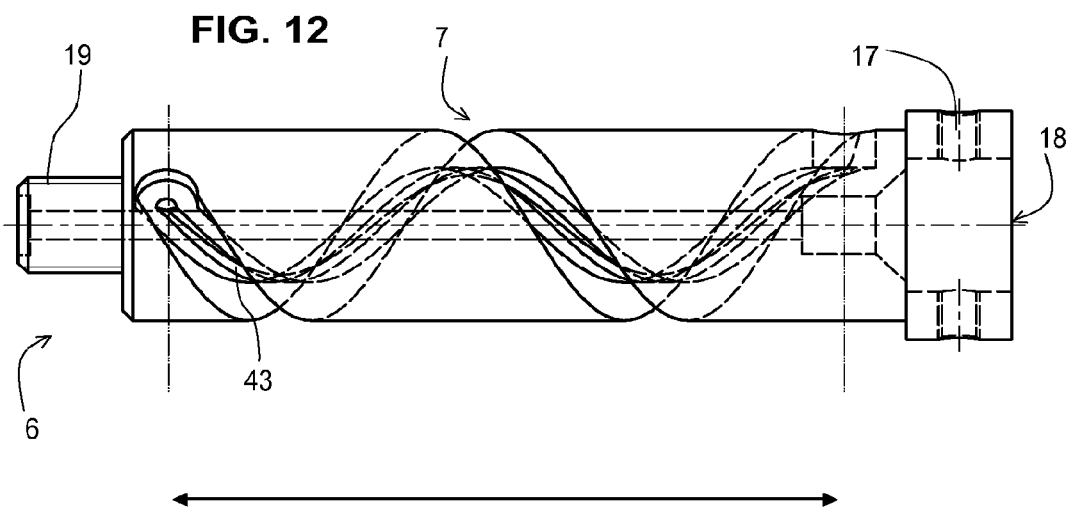
FIG. 12 is a schematic side view of a cylindrical threaded element of one example.
Figure 13:
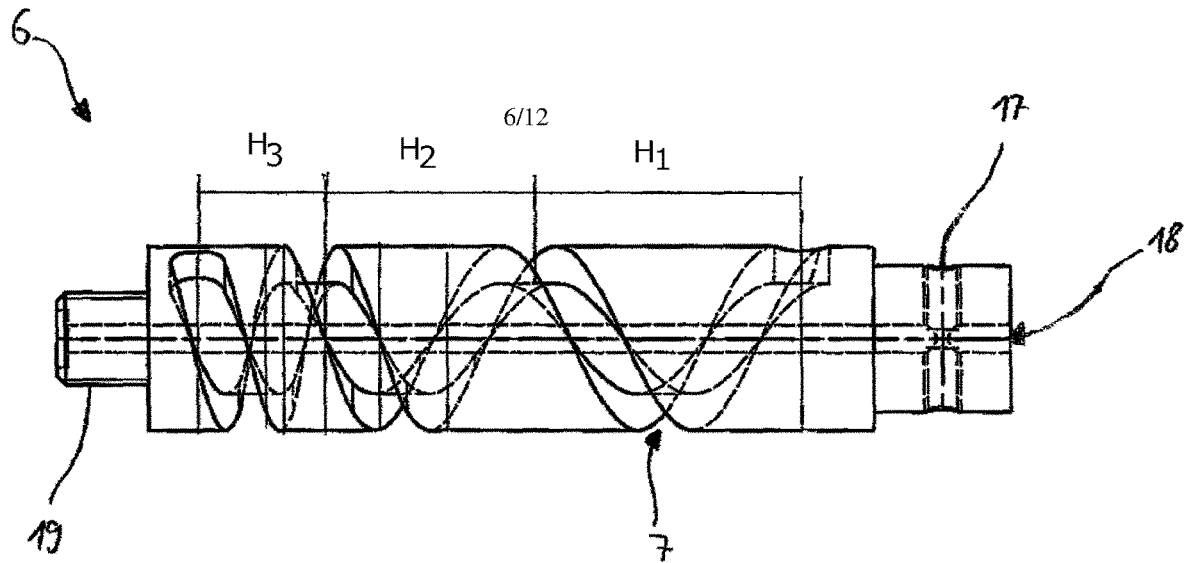
FIG. 13 is a schematic side view of a cylindrical threaded element of a further example.

FIGS. 12 and 13 show different examples of the cylindrical threaded element 6 usable in the first embodiment. The example of FIG. 12 is shown used in the handle of FIG. 2, and the example of FIG. 13 is shown used in the handle of FIG. 5, but this selection is merely for the sake of illustration, and either example of element 6 may selected for each handle as desired.

Both examples of cylindrical threaded elements 6 comprise an internal lumen 18 through which tube member 3 and/or a guide wire may be inserted. Connection element 17 allows to connect the cylindrical threaded element 6 to an actuation means such as the rotary handle 5. An additional axle member 19 allows to rotationally connect member 6 to further elements and/or to the handle 4. The cylindrical threaded element 6 comprises thread 7. The thread 7 may have any suitable cross-section form, such as rectangular (as in FIG. 13) or rectangular with an additional guide-groove 43 (FIG. 12) for co-operating with a tip of the pin 8.

The element 6 is configured to drive linear translation of the sheath 2 between operative closed and open positions, over a full operative range of linear movement, by three turns or less about the catheter axis. In FIG. 12, the full operative range of movement is achieved by two turns or less. In either case, a friction member 45 (FIG. 2) may optionally be provided to resist self-rotation that might otherwise occur when using a relatively coarse thread 7 to achieve such translation for few rotational turns. The friction member 45 may be positioned between confronting surfaces of the rotary control 5 and the handle 4. For example, the friction member 45 may be mounted in a groove on the outer surface of the handle 4 for bearing against an inner surface of the rotary control 5. The friction member 45 may comprise an O-ring of elastomeric material. Such an arrangement can provide reliable and reproducible control over the amount of friction between the handle 4 and the rotary control 5, and facilitate simple construction.

In the example of FIG. 12, thread 7 has a substantially uniform thread pitch. Such a thread 7 produces uniform gearing between the rotary control 5 and the sheath 2 over the entire range of movement. In the alternative example of FIG. 13, thread 7 has three sections with different thread pitches H1, H2 and H3. The different thread pitches H1, H2 and H3 allow having different gearing ratios between the movement of the actuation means 5 and the movement of the sheath 3. Alternatively, the member 6 may also comprise further sections with yet different thread pitches. For example, further intermediate sections may define a progressive incremental change in thread pitch (e.g., between H1 and H2) in order to avoid large step changes or discontinuities in the thread smoothness. The different thread pitches may be in the range of about 5 mm to about 50 mm, including, for example, about 10 mm to about 40 mm, about 15 mm to about 30 mm, or about 5 mm to about 35 mm. Table 1 shows an example of different thread pitches which may be used for the thread 7 of the cylindrical threaded element 6:

TABLE-US-00001 TABLE 1 Thread Thread pitch section [mm] H1 30 H2 10 H3 15

Figure 4:
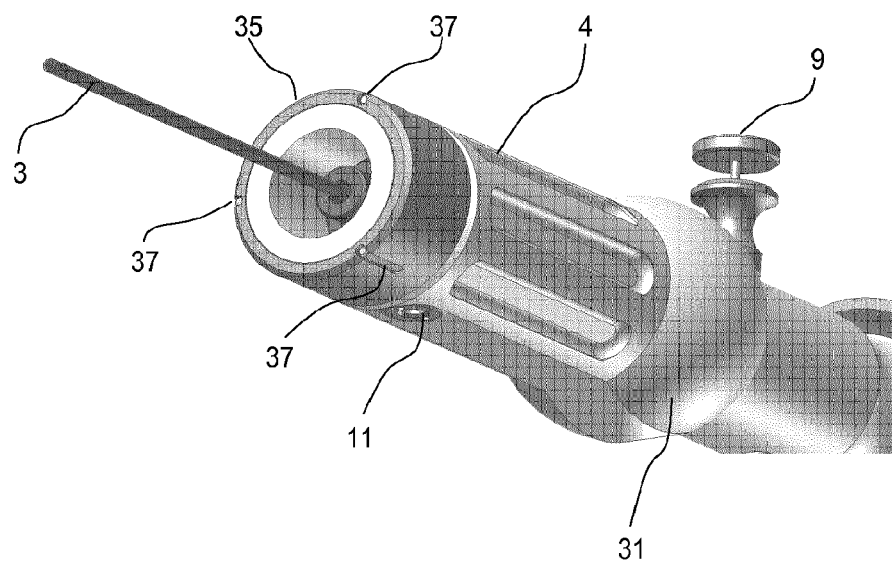
FIG. 4 is a schematic perspective view from below the proximal end (without the sheath represented).
Figure 5:
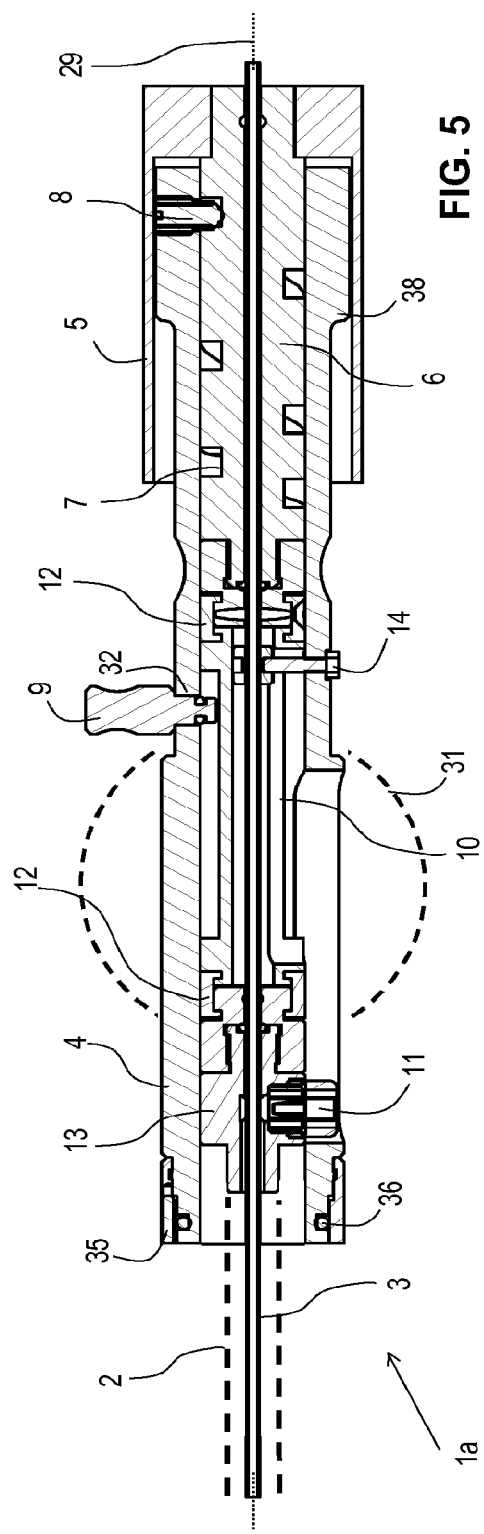
FIG. 5 is a schematic section showing a modified form of a handle usable with the first embodiment.

Referring to the different thread pitches H1, H2 and H3 of thread 7 as shown in FIG. 13, and the stent example shown in FIG. 14, the thread pitch H1 is configured such as to provide a first transmission or gear ratio when moving the distal end of the sheath 3 along the first portion S1 of the stent 15. Accordingly, the thread pitch H2 is arranged such as to provide a different second transmission or gear ratio, such as a lower second transmission or gear ratio when the distal end of the sheath 2 moves along portion S2 of the stent 15. Finally, thread pitch H3 may be adapted such as to provide yet a different third transmission or gear ratio when the distal end of the sheath 2 moves along the portion S3 of the stent 15. The diagrams (a) and (b) in FIG. 4 illustrate two alternatives examples for the portions S1, S2 and S3; it will be appreciated that other configurations are also possible.

Figure 15:
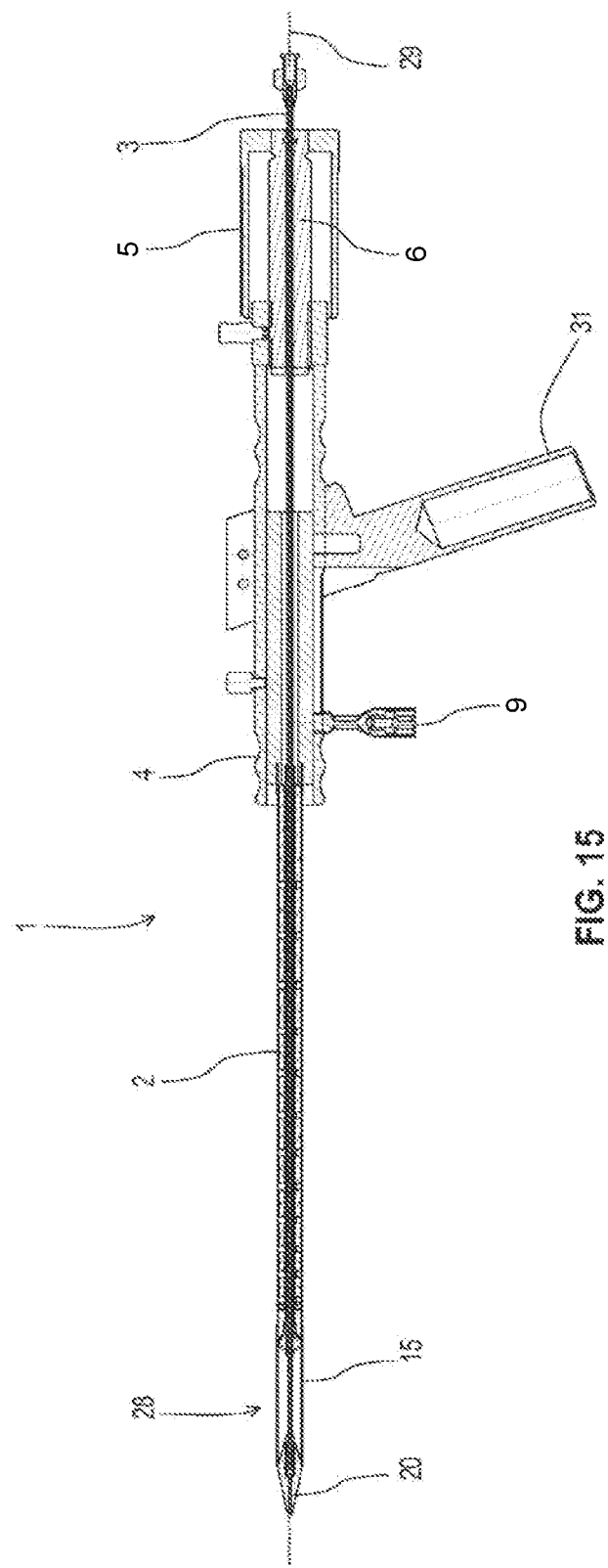
FIG. 15 is a schematic section illustrating a second embodiment of a delivery catheter according to the disclosure.
Figure 1G:
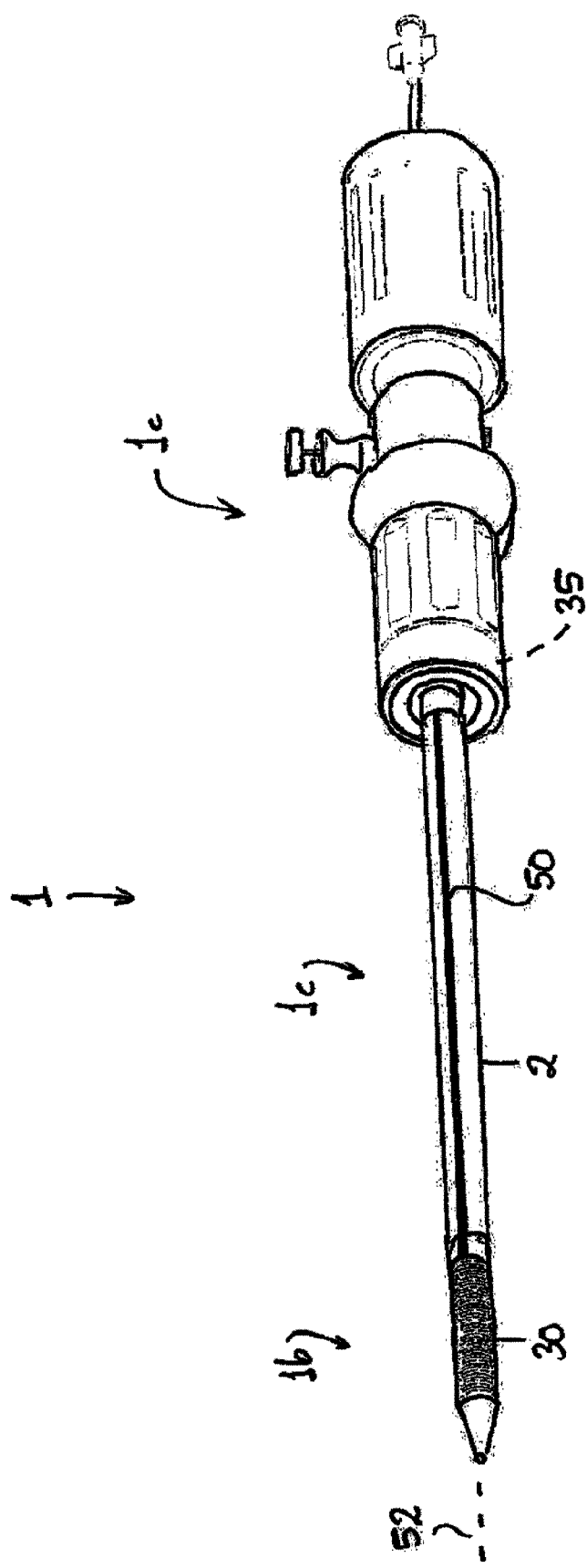

FIG. 15 shows an alternative embodiment 1 of the catheter delivery device 1 according to the present disclosure. A stent attachment region 28 is located at the distal end of the catheter device. At its most distal tip, the conical section 20 is arranged. The sheath 2 extends from the handle 4 located at the proximal end of the catheter device 1 to the distal end. As such, the sheath 2 may at least partially or completely circumferentially cover the stent 15. Tube member 3 extends along the entire length of the delivery device 1 and comprises a guide wire 29. The handle 4 comprises a pistol grip 31 to enable a safe and easy handling of the catheter device by an operator. The catheter delivery device 1 further comprises braking means 5 configured as cylindrical threaded element 6. The threaded element may optionally include a thread 7 with different thread pitches, which applies a resistance to the actuation means 5 having a braking effect. If the pitch becomes lower, the force which has to be applied by the braking means 5 becomes greater or turning becomes impossible so that the movement is stopped. Alternatively, the thread pitch may be uniform, and the braking effect (increased) resistance may be created by a sliding member to which the sheath is attached. For example, the sliding member may slide in a proximal direction freely or substantially "unbraked" over a first movement range to a predetermined position without contacting the thread; when the sliding member reaches the predetermined position, the sliding member abuts the thread, such that the braking effect is applied for the remainder of the range of proximal movement.

Referring to FIGS. 16-23 and 26-29, in some embodiments, the delivery catheter 1 further comprises at least one radio-opaque indicator 50 and/or 54/56 and/or 80/82 for indicating a position or orientation of the delivery catheter, or a portion thereof, or a stent (e.g. stent-valve) carried by the delivery catheter. For example, the radio-opaque indicator may indicate a rotational orientation of the delivery catheter and/or stent-valve 15 and/or stent holder when observed using medical-imaging (e.g. fluoroscopy) during implantation of a stent. The radio-opaque indicator may be used with, or without, the indicator ring 35.

In a similar manner for the optional indicator ring 35, such a radio-opaque indicator 50/54/56/80/82 can provide the operator with valuable information about the rotational orientation with respect to the native anatomy. This can enable the operator, if desired, to be able to orientate the catheter 1 and/or stent 15 with respect to the native anatomy, even if individual stent features, or the stent orientation, are not easy to identify from the stent alone. For example, the stent 15 in its collapsed or compressed form, may be so small and/or so deformed compared to its expanded configuration, that the orientation may be difficult to discern from the stent alone. In some embodiments, the stent may be a stent-valve 15, and the radio-opaque indicator(s) may be configured to enable the operator to discern whether (or when) the stent-valve is in a certain alignment with native valve anatomy. The radio-opaque indicator(s) may be configured to be aligned with at least one commissural section of the stent-valve.

In some embodiments, at least one visual indicator 50 also provides a visual indication of the same rotational orientation as the radio-opaque marker(s). For example, the visual indicator may have a distinctive colour. At least one radio-opaque indicator 50 and at least one visual indicator may be provided by the same material and/or element 50 of the delivery catheter. At least a portion of the indicator 50 outside the body may, for example, be observed visually. At least a portion of the (e.g. same) indicator 50 within the body may, for example, be observed by virtue of its radio-opaque property and using medical imaging.

As may be seen in FIG. 16, in some embodiments, the radio-opaque indicator 50 may comprise a feature that is substantially elongate in an axial direction of the delivery catheter 1. For example, the indicator 50 may be or comprise an elongate line extending in a direction parallel to an axis 52 of the catheter. The line may optionally be offset from the axis 52 of the catheter.

In some embodiments, the radio-opaque indicator 50 may be provided on, or comprised as part of, a stem portion 1*c* of the delivery catheter 1, extending at least between a proximal portion 1*a* of the delivery catheter (for example, a handle portion for manipulation by an operator) and a distal portion 1*c* (for example, the stent accommodation region 30).

As may be seen from FIGS. 17 and 18, in some embodiments, the radio-opaque marker 50 may be formed by co-extrusion of radio-opaque material with plastics tubing for forming a component 2 (or 2*a* or 2*b* or 2*c*) of the delivery catheter 1. The component may, for example, be the stem portion 1, or the tubing 2 or 2*a* referred to above. An example radio-opaque material suitable for co-extrusion is, for example, barium sulphate and/or bismuth oxide.

In some embodiments, the rotational orientation of the stent 15 may be invariable (for example, if the orientation of the stent is determined by the stent-holder, and the orientation of the stent-holder is fixed with respect to the remainder of the delivery catheter 1). In such case, the radio-opaque indicator may have a fixed orientation (for example, at least with respect to the stent-holder). For example, the radio-opaque indicator may be aligned with an attachment feature, such as a pin, projection or recess, for mating engagement with an attachment element of the stent-valve. The radio-opaque indicator may be aligned with a commissural feature (e.g. commissural section or commissural post section) of the stent-valve when loaded in the delivery catheter.

In some other embodiments, the rotational orientation of the stent 15 may be variable (in a similar to situation described above in respect of the adjustable indicator ring 35). For example, the stent may have a variable or non-predetermined orientation with respect to a stent holder of the attachment region. Additionally or alternatively, the stent holder may have a non-predetermined orientation with respect to the handle. However, although the orientation may be non-predetermined, it may be unlikely to change after loading of the stent into the delivery catheter. The orientation may be visible during and/or following loading, allowing the position of the radio-opaque indicator 50 or the component carrying the indicator 50 to be set manually to provide an indication useful for the implantation procedure. In some embodiments, the component 2 carrying the radio-opaque indicator 50 may be rotatably adjustable in a similar manner to, and/or in unison with, the indicator ring 35 if used.

FIGS. 19-22 illustrate a further example of delivery catheter with at least one radio-opaque indicator 50 or 54/56, optionally two indicators 50 and 54/56.

The first indicator 50 may be similar to that described in the preceding example. For example, the first indicator 50 may be an elongate feature, optionally co-extruded as part of the tubular component 2. In the form shown, the first indicator 50 may be arranged substantially at a surface portion of the tubular component 2 (for example as seen in FIGS. 19 and 20). The first indicator 50 may be substantially smooth and integrated as part of the round cross-section shape of the component 2.

Additionally or alternatively, the second radio opaque indicator 54/56 may comprise a feature 54. The feature 54 may extend generally circumferentially around the axis of the delivery catheter, and/or may extend predominantly circumferentially, and/or may be split-ring shaped, and/or may be C-shaped, and/or have an axial extent of less than about 5 mm.

Whatever the shape, in some embodiments, the axial extent of the feature 54 may be any one or more of: less than about 5 mm; less than about 4 mm; less than about 3 mm, less than about 2 mm; between about 1 mm and about 2 mm.

The feature 54 may include one or more patterns defining a rotational orientation. For example, the pattern(s) may be interruption(s) or discontinuity(ies) 56 in the circumferential extent of the feature 54, or axial extension(s) or projection(s) of the feature 54.

The second indicator 54 may be a metal or metal alloy that is carried on or integrated in the delivery catheter, for example, in or on a sheath (or constraining portion) 2a for covering the stent accommodation region 30. An example radio-opaque metal alloy is, for example, an alloy comprising at least one of platinum and iridium, optionally both (e.g. platinum-iridium alloy). The metal or metal-alloy may, for example, be provided in generally flat strip form (e.g. a band or split band), or in other forms such as a wire.

In the illustrated example, a combination of the first elongate feature 50, and the second circumferential feature 54 may be provided. The second feature 54 may have an interruption 56 that is offset from the first feature 50 (for example, circumferentially by about 180 degrees). The offset may enhance the ease with which the rotational orientation can be discerned using, for example, fluoroscopy or X.ray imaging. For example, if the interruption 56 cannot be seen (or e.g. cannot be seen clearly) in the image, then it may be in the background (e.g. obscured by the foreground), indicating that the first feature 50 is in the foreground; alternatively, if the interruption 56 can be seen (or e.g. can be seen clearly), then the interruption 56 may be in the foreground, and the first feature 50 in the background. Additionally or alternatively, by turning the delivery catheter in one direction, the corresponding movement in the fluoroscopic image can be observed to indicate which feature (e.g. the first feature 50 or the interruption 56 in the second feature 54) is in the foreground, and which is in the background.

Although the illustrated example shows two radio-opaque indicators 50 and 54/56 used in combination, in some embodiments, either one of the indicators 50 or 54/56 may be omitted if desired (e.g. leaving only the other indicator).

Referring still to FIGS. 19 to 22, in some embodiments, the sheath (or constraining portion) 2a may comprise a mouth portion 60 with a peripheral edge 62.

Additionally or alternatively to any rotational orientation indication, the radio-opaque indicator 54/56 may be incorporated at or near the mouth region (mouth portion) 60 of the sheath 2a to provide an indication of the axial position of the sheath 2a. For example, the radio-opaque indicator 54/56 may be provided within about 5 mm of the peripheral edge 62 of the mouth portion 60, optionally within about 4 mm of the peripheral edge 62, optionally within about 3 mm of the peripheral edge 62. In some embodiments, a slight spacing away from the peripheral edge 62 may be desired, as explained below.

A second region (second portion) 64 of the sheath (or constraining portion) 2a may extend away from the mouth portion 60, for example, proximally towards the handle (with reference to FIGS. 1-9). The mouth portion 60 and the second portion 64 may have different characteristics. For example, the mouth portion 60 may be configured to be able to flare towards its peripheral edge 62 (as indicated by the broken line 66 in FIG. 19). The mouth portion 60 may flare when subjected to a radial expansion force exerted by a stent (stent-valve) when the mouth portion 60 overlaps the stent. Optionally, the mouth portion 60 may return to or towards a non-flared configuration when the radial expansion force is removed. The second portion 64 may be configured substantially not to flare, or at least to flare less than the mouth portion 60, when subjected to such a radial expansion force.

The radio-opaque indicator 54/56 may be configured to permit flaring of the mouth portion 60, and/or configured so as not to hinder substantially such flaring. For example, the circumferential interruption or discontinuity 56 may permit flaring, by reducing the bracing effect of the indicator 54 compared to a closed-loop shape of metal ring body. Additionally or alternatively, a spacing of the indicator 54 away from the peripheral edge 62 may permit flaring of the mouth portion 60, especially at the peripheral edge 62. For example, the indicator 54 may be spaced from the peripheral edge by at least about 1 mm, optionally at least about 2 mm, optionally at least about 3 mm.

The radio-opaque indicator 54 may have an axial extent of less than about 5 mm; less than about 4 mm; less than about 3 mm, less than about 2 mm; between about 1 mm and about 2 mm. Such a dimension may further contribute to facilitating flaring of the mouth portion 60 and/or to accuracy of position indication of the mouth portion 60.

The ability of the mouth portion 60 to flare towards its peripheral edge 62 may facilitate translation of the sheath 2a over a stent (stent-valve), for example, during loading or re-sheathing of a stent (stent-valve) in use. The flared shape may reduce or avoid force concentration between the stent (stent-valve) and the sheath at the peripheral edge. Instead, a gradual contact region may distribute the contact force along the mouth portion, to the second portion. A high force concentration may be undesirable in case this might otherwise damage the stent (stent-valve) and/or the sheath in use.

FIG. 23 shows one example of structure of the mouth portion 60 and the second portion 64. The sheath 2a may generally be formed as a laminate, including first and second layers 70 and 72. The first layer 70 may be a radially inward of the second layer 72, or vice versa. Optionally, one of the layers, e.g. first layer 70, may be generally continuous and/or uniform across both the mouth portion 60 and the second portion 62. Additionally or alternatively, one of the layers, e.g. second layer 72, may be generally discontinuous and/or non-uniform between the mouth portion 60 and the second portion 62. For example, the second layer 72 may comprise a softer or more easily deformable polymer in the mouth region 60 than in the second region 64. Additionally or alternatively, the second layer 72 may have a different thickness to provide the different characteristics.

In the mouth region 60, the radio-opaque indicator 54 may be embedded between the layers 70 and 72 of the laminate structure.

Additionally or alternatively to the above, the second portion 64 may have a radial or circumferential reinforcement, such as a coil reinforcement, to provide a different characteristic from the mouth region 60. Optionally, the mouth region 60 has no reinforcement. In other embodiments, both the mouth region 60 and the second region 62 have no reinforcement.

Referring to FIGS. 24-26, a further example of radio-opaque indication is illustrated. This may optionally be used in combination with the radio-opaque indicator(s) described above with respect to of FIGS. 16 to 18 and/or to FIGS. 19-23, or optionally independently of those described above.

FIG. 24 may illustrate a detail of the tube member 3, similar to FIG. 7 above. The tube member (also referred to herein as tubing) 3 may carry a stent holder (also referred to herein as coupling means) 16. The tube member 3 may carry an indicator 84, optionally positioned adjacent to the stent holder 16, optionally in contact with the stent holder 16, or optionally spaced from the stent holder 16. The indicator 84 may be distinct from the stent holder 16 and/or non-integral with the stent holder 16. Such an arrangement may permit the indicator 84 to be observed more easily in the image produced by medical viewing apparatus, distinct from the relative clutter of the stent holder 16 and attached stent of the stent-valve (as best seen in FIGS. 25 and 26). It may also permit the indicator 84 to be of a material different from the stent-holder 16, and/or be mounted on the tube member 3 by a different mounting technique from that used for the stent holder 16.

The indicator 84 may comprise at least one, optionally two or more, radio-opaque indicators or features 80 and 82, referred to hereinafter as indicators although it will be understood that the same explanation applies to plural features of the same indicator if desired. In the illustrated example, the radio-opaque indicators 80 and 82 may be of different axial lengths, so as to be easily distinguishable from each other in a medical imaging view. The radio-opaque indicators 80 and 82 may be carried in or by a hub or sleeve 86. The sleeve may be of non-radio-opaque material, for example, of radio-transparent plastics, so as not to hinder observation of the indicators 80 and 82.

The sleeve 86 may, for example, be secured around the tube member 3 by any suitable technique, for example, by adhesive. In some embodiments, when in use, the sleeve 86 might not be expected to have to withstand substantial loads, especially if the indicator is distinct or non-integral with the stent holder 16.

Referring to FIG. 25, a rotational alignment relation is illustrated between (i) the radio-opaque indicators or features 80/82, (ii) the stent-valve 15 attached to the stent holder 16, and (iii) a desired orientation with respect to a native anatomy of an aortic valve.

A first, e.g. axially "long", indicator/feature 80 may be generally aligned with an angular feature of the stent holder 16. For example, the first indicator 80 may be aligned with an attachment region of the stent holder 16, so as to be aligned with a commissural region of the stent-valve 15 when attached to the stent holder 16. A second, e.g. axially "short", indicator/feature 82 may be angularly offset from the first indicator 80 by a predetermined angle. Optionally, the angle is about, and/or is substantially, 90.degree.. Alternatively, the second indicator 82 may be aligned with a second angular feature of the stent holder.

If desired, the long and short lengths may alternatively be swapped between the indicators 80 and 82, such that the second indicator 82 is the longer, and the first indicator 80 is the shorter.

During implantation, it may be desirable to align commissural regions of the stent valve 15 with commissures of the native valve. The three native valve leaflets are labelled in FIG. 25 as LCC (left coronary cusp), RCC (right coronary cusp), and NCC (non coronary cusp). With typical medical imaging equipment (e.g. fluoroscopy equipment) used during an implantation procedure, it is possible to obtain an orthogonal projection of the aortic root with the RCC positioned appropriately between the LCC and NCC. By observing the indicators 80 and 82 in the, e.g., fluoroscopic, image, the alignment of the stent-valve 15 relative to the native valve anatomy may be assessed, and the catheter rotated as desired to achieve a desired rotational alignment.

For example, as seen in FIG. 25, in a desired rotational alignment, the first (e.g. long) indicator 80 may be positioned at a "6-oclock" position, corresponding to the commissure between the NCC and the LCC. In the orthogonal projection image, the first indicator 80 may be seen to be central, or "on-axis". Depending on the type of guidewire 90 used in the procedure, the on-axis or central position of the first indicator 80 may be directly visible if the guidewire 90 is itself nonradio-opaque (as in FIG. 25), or the first indicator 80 may be masked by the guidewire 90 if the guidewire 90 itself is radio-opaque (as in FIG. 26). In the latter case, the merging of the first indicator 80 with the guidewire 90 nevertheless provides an accurate indication of the first indicator 80 being "on axis" or centre-positioned.

Referring to FIG. 25, the second (e.g. short) indicator 82 may be positioned to one side, for example, at a "9-oclock" position. The additional information provided by the second indicator 82 may be significant, because it allows the operator to verify that the first indicator 80 is indeed at the "6-oclock" position, and not at a "12-oclock" position, which may also resemble an "on-axis" position of the first indicator 80 in a two-dimensional projection, but be a false alignment with respect to the native anatomy. Were the first indicator to be accidentally in a "12-oclock" position, the second indicator 82 would be visible on the opposite side of the axis in a "3-oclock" position, from which the operator may deduce that the alignment is false. The combination of the first and second indicators 80 and 82 together may enable the rotational alignment of the stent holder 16 and/or the stent valve 15 to be viewed and assessed unambiguously despite a two-dimensional projection in the fluoroscopic view of the three-dimensional native anatomy.

Other relative positions and angles of the first and second indicators/features 80 and 82 may be used as desired.

Figure 27:
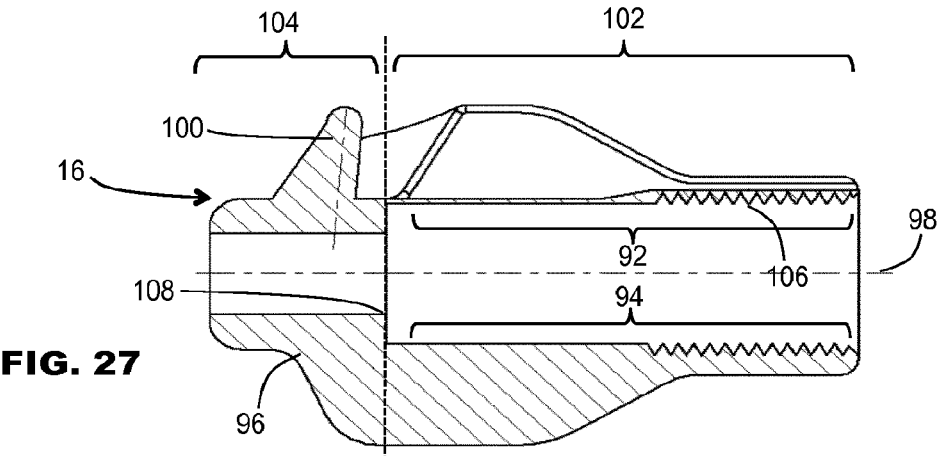
FIG. 27 is a schematic cross-section showing a stent holder in isolation.
Figure 28:
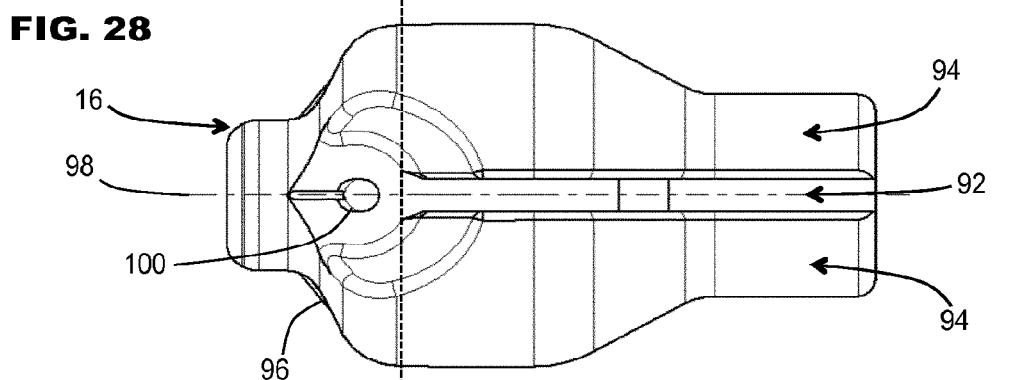
FIG. 28 is a top view of the stent holder of FIG. 27.
Figure 29:
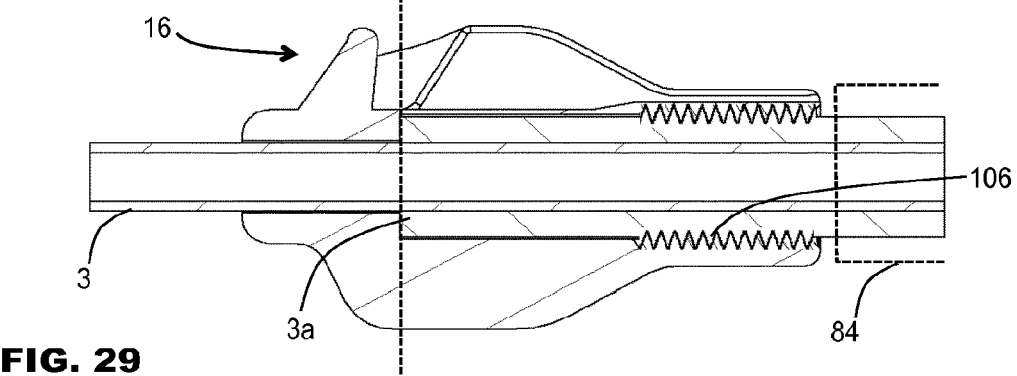
FIG. 29 is a schematic cross-section showing the stent holder crimped to support tubing.

FIGS. 27-29 illustrate a further example, including a configuration of the stent-holder 16. This example may optionally be used with any of the foregoing examples, for example, as described with reference to FIGS. 24-26.

Referring to FIGS. 27-29, the stent holder 16 may be configured to be attached to the tube member (also referred to herein as tubing or support tubing) 3 by a crimp connection. The tube member 3 may have a dual-walled construction as indicated at 3a (as described previously).

The stent holder 16 may comprise one or more crimp zones 92 and one or more non-crimp zones 94/96. The crimp zones 92 may alternative with non-crimp zones 94 around an axis 98 of the stent holder 16 over at least a portion of an axial length of the stent holder. At one axial end of the stent holder 16, for example corresponding to or axially overlapping with attachment regions 100 (described below), the stent holder 16 may optionally comprise only a non-crimp zone 96, for example, a circumferentially continuous non-crimp zone 96.

The one or more crimp zones 92 may have a substantially thinner all thickness than the one or more non-crimp zones 94 and/or 96. During assembly of the stent holder 16 to the tube member 3, the stent-holder 16 may be crimped by a suitable tool, causing the crimp zones 92 to fold and/or collapse circumferentially. This enables the stent holder 16 to collapse around or on to the surface of the tube member 3 in a controlled manner, without distorting the shape and structure of the stent-holder 16 in non-crimp zones 94 and/or 96.

In the present example, the stent holder may comprise three crimp zones 92 spaced apart in the circumferential direction by three non-crimp zones 94 to define a first region 102 of the stent holder. A second region 104 at one end of the stent holder 16 may be defined by an annular non-crimp zone 96. During the crimping operation to assemble the stent holder 16 to the tube member 3, the second region 104 may remain substantially undeformed and/or non-collapsed. The first region 102 may deform or collapse, at least partly progressively, in an axial direction away from the second region 104.

The stent holder 16 may comprise one or more interior surface regions 106 having a non-smooth surface and/or non-smooth profile that grips the tube member 3. For example, the non-smooth surface 106 may bite against and/or bite into the tubing. The regions 106 may optionally be provided in the crimp zone(s) 92 and/or in the non-crimp zone(s) 94. The non-smooth surface 106 may optionally comprise one or more of: projections; corrugations, teeth (e.g. individual teeth, or one or more elongate fins having a pointed section shape or a pointed tip); a helical thread. Other non-smooth surface configurations 106 are also envisaged.

The crimp connection may retain the stent holder 16 in a fixed position, axially and/or rotatably, with respect to the tubing. A crimp connection may provide a reliable and firm connection using low-cost materials, and be load-bearing to withstand significant forces between the tubing and the stent holder in use (for example, significant forces during crimping of a stent-valve around the tubing, and/or during re-collapsing of a partially expanded stent-valve for "recapture" during an implantation procedure).

The interior profile of the stent holder 16 may optionally include a step 108 (for example, corresponding to the interface between the first and second regions 100 and 102). The step 108 may define an axial stop in register with the transition between the previously described dual-walled and single-walled structures of the tube 3, indicated at 3a. This facilitate the assembly process by self-positioning of the stent holder 16 on the tube member 3, and ensure that the crimp connection at the surface 106 occurs against the stronger dual-wall structure.

The tube member 3 may be of plastics and/or polymeric material. Additionally or alternatively, the stent-holder 16 may be of metal (or metal alloy); or the stent holder 16 may be of plastics and/or polymeric material.

As illustrated in FIG. 29, the indicator 84 described above may be positioned, distinct from but adjacent to the stent holder 16. The indicator 84 may be secured to the tube 3 by any suitable technique, optionally non-loading bearing, and optionally different from the crimp connection of the stent holder 16 to the tube member 3. For example, the indicator 84 may be secured to the tube member 3 by adhesive.

Mounting the indicator 84 independently of the stent-holder 16 may also facilitate the crimp connection between the stent holder 16 and the tube member 3 so close to the indicator 84. It will be appreciated that were the indicator 84 to be integrated with the stent holder 16, such crimping of the stent-holder 16 immediately adjacent to the indicator 84 might not be feasible so easily without risking distortion of the indicator 84, leading to potentially inaccurate rotational position indication.

Definitions

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the disclosure will be apparent from the following detailed description and claims.

For the purposes of promoting an understanding of the embodiments described herein, reference will be made to preferred embodiments and specific language will be used to describe the same. The terminology used herein is for the purpose of describing particular embodiments only, and is not intended to limit the scope of the present disclosure. As used throughout this disclosure, the singular forms "a," "an," and "the" include plural reference unless the context clearly dictates otherwise. Thus, for example, a reference to "a device" includes a plurality of such devices, as well as a single device.

Throughout this application, the term "about" is used to indicate that a value includes the standard deviation of error for the device or method being employed to determine the value.

Reference to numeric ranges throughout this specification encompasses all numbers falling within the disclosed ranges. Thus, for example, the recitation of the range of about 1% to about 5% includes 1%, 2%, 3%, 4%, and 5%, as well as, for example, 2.3%, 3.9%, 4.5%, etc. In some instances in the specification the term "inclusive" is used to reiterate this point.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

What is claimed:

1. A delivery catheter for a stent, comprising:
an elongate shaft having a distal end with a tapered nose cone, a proximal end, and a stent receiving region adjacent the distal end;
a stent holder disposed at a proximal end of the stent receiving region, the stent holder defining a stent attachment region configured to engage an end of the stent; and at least one radio-opaque indicator for indicating a rotational position of the stent holder, the at least one radio-opaque indicator fixed to a distal region of the elongate shaft proximally adjacent to and spaced apart from the stent holder, the at least one radio-opaque indicator including a first radio-opaque indicator defining an elongate axial line disposed at a single circumferential position and circumferentially aligned with the stent attachment region of the stent holder, wherein the stent attachment region is positioned between the at least one radio-opaque indicator and the nose cone.

2. The delivery catheter of claim 1, wherein the stent attachment region is configured to engage an inflow end of the stent with a remainder of the stent extending towards the nose cone.

3. The delivery catheter of claim 1, wherein the stent receiving region is between the stent holder and the nose cone.

4. The delivery catheter of claim 1, further comprising a sheath translatable between a closed position at least partly covering the stent receiving region and an open position not substantially covering the stent receiving region.

5. The delivery catheter of claim 4, wherein the sheath is configured to move in an upstream direction when moving from the closed position to the open position.

6. The delivery catheter of claim 4, wherein the sheath includes a mouth region configured to flare in response to a radially outward force exerted thereon from the stent at the stent receiving region.

7. The delivery catheter of claim 6, wherein a second region of the sheath is configured substantially not to flare in response to the radially outward force exerted thereon from the stent at the stent receiving region.

8. The delivery catheter of claim 1, wherein the at least one radio-opaque indicator has an axial extent selected as at least one from: less than about 5 mm; less than about 4 mm; less than about 3 mm, less than about 2 mm; between about 1 mm and about 2 mm.

9. The delivery catheter of claim 1, wherein the at least one radio-opaque indicator comprises metal or metal alloy.

10. The delivery catheter of claim 9, wherein the metal alloy comprises at least one of platinum and iridium.

11. The delivery catheter of claim 1, wherein the first radio-opaque indicator is substantially elongate in an axial direction parallel to a longitudinal axis of the elongate shaft.

12. The delivery catheter of claim 11, further comprising a second radio-opaque indicator that is substantially elongate in the axial direction parallel to the longitudinal axis of the elongate shaft.

13. The delivery catheter of claim 12, wherein the second radio-opaque indicator is distinct from the first radio-opaque indicator by one or more selected from: (i) being spaced angularly from the first radio-opaque indicator; (ii) being spaced axially from the first radio-opaque indicator; (iii) having a size different from the first radio-opaque indicator; and (iv) having a length different from the first radio-opaque indicator.

14. The delivery catheter of claim 13, wherein the first and second radio-opaque indicators are both adjacent to but spaced apart axially from the stent holder.

15. The delivery catheter of claim 12, further comprising a sleeve carrying the first and second radio-opaque indicators, the sleeve being distinct from the stent holder.

16. The delivery catheter of claim 12, wherein the first and second radio-opaque indicators have different lengths and the second radio-opaque indicator is spaced apart circumferentially around the longitudinal axis of the elongate shaft from the first radio-opaque indicator.

17. A delivery catheter for a stent, comprising:
an elongate shaft having a distal end with a tapered nose cone, a proximal end, and a stent receiving region adjacent the nose cone;
a stent holder configured to engage an end of the stent; and
first and second radio-opaque indicators fixed to a distal region of the elongate shaft for indicating a rotational position of the stent holder, the first and second radio-opaque indicators each being an elongate axial line circumferentially spaced apart from one another and proximally adjacent to and spaced apart from the stent holder, wherein the stent holder is positioned between the first and second radio-opaque indicators and the nose cone.

18. The delivery catheter of claim 17, wherein the stent holder is configured to engage an inflow end of the stent with a remainder of the stent extending towards the nose cone.

19. The delivery catheter of claim 17, wherein the first and second radio-opaque indicators have different lengths.

20. A delivery catheter for a stent, comprising:
an elongate shaft having a distal end with a tapered nose cone, a proximal end, and a stent receiving region adjacent the distal end;
a stent holder disposed at a proximal end of the stent receiving region, the stent holder defining a stent attachment region configured to engage an end of the stent; and
first and second elongate radio-opaque indicators fixed to a distal region of the elongate shaft for indicating a rotational position of the stent holder, the first and second radio-opaque indicators each being an elongate axial line disposed at a single circumferential position and proximally adjacent to and spaced apart from the stent holder, the first and second radio-opaque indicators having different lengths, wherein the stent holder is positioned between the first and second radio-opaque indicators and the nose cone.

* * * * *